US 7,381,215 B2

(12) United States Patent
Boute

(10) Patent No.: US 7,381,215 B2
(45) Date of Patent: Jun. 3, 2008

(54) SYSTEM AND METHOD FOR DETERMINING AN EFFECTIVENESS OF A VENTRICULAR PACING PROTOCOL FOR AN IMPLANTABLE MEDICAL DEVICE

(75) Inventor: Willem Boute, Dieren (NL)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 11/039,763

(22) Filed: Jan. 21, 2005

(65) Prior Publication Data

US 2006/0167507 A1    Jul. 27, 2006

(51) Int. Cl.
*A61N 5/06*    (2006.01)
(52) U.S. Cl. ........................................................ 607/90

(58) Field of Classification Search .................... 607/4, 607/14, 17–19, 90
See application file for complete search history.

(56) References Cited

U.S. PATENT DOCUMENTS 6,772,005 B2 *    8/2004    Casavant et al. ............... 607/4

\* cited by examiner

*Primary Examiner*—George Manuel
(74) *Attorney, Agent, or Firm*—Daniel G. Chapik

(57) ABSTRACT

An implantable medical device operates to promote intrinsic ventricular depolarization according to a pacing protocol. The medical device monitors the number of attempts made to promote intrinsic conduction in comparison with the number of successful cardiac cycles to determine an efficiency value.

20 Claims, 15 Drawing Sheets

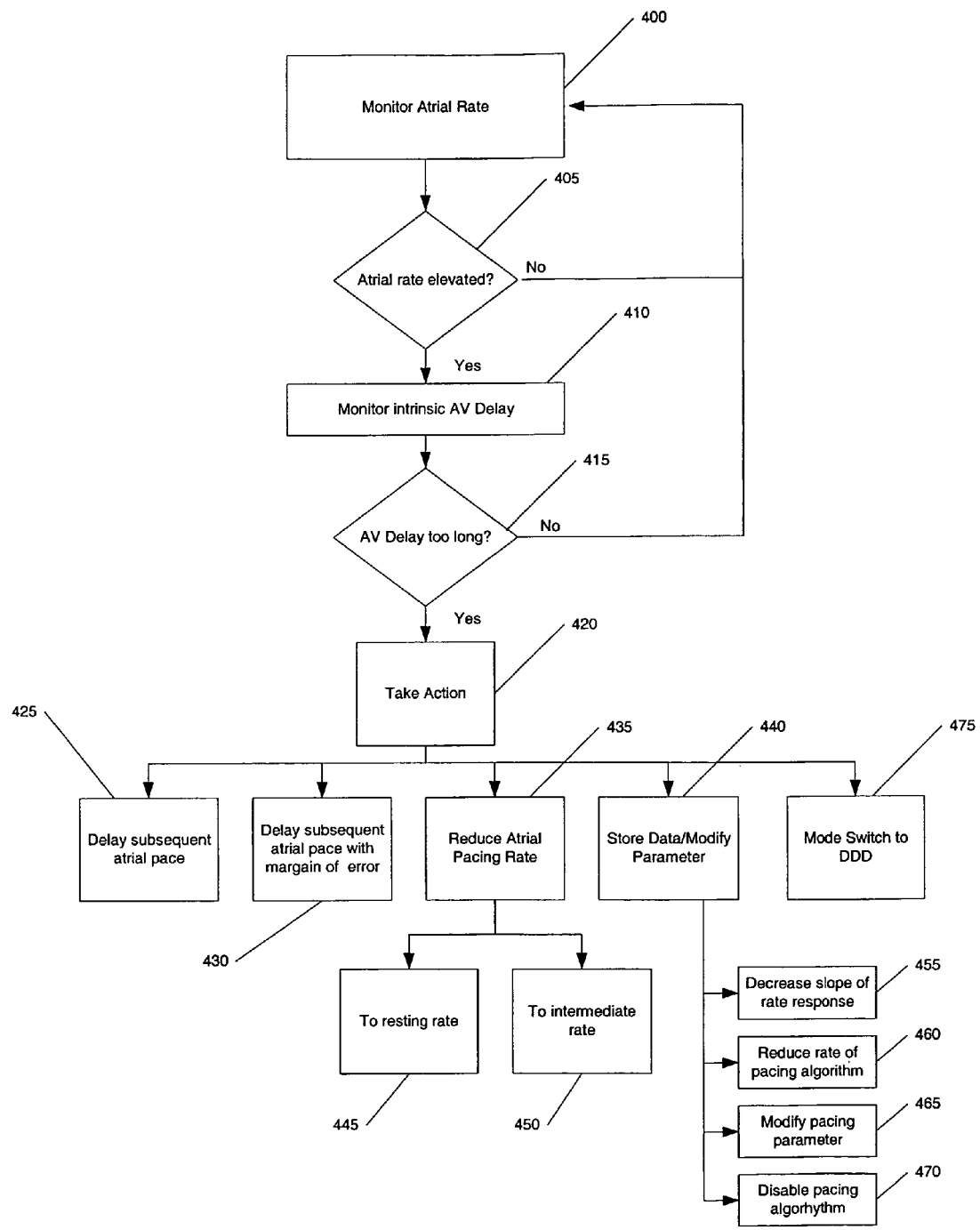

SYSTEM AND METHOD FOR DETERMINING AN EFFECTIVENESS OF A VENTRICULAR PACING PROTOCOL FOR AN IMPLANTABLE MEDICAL DEVICE

FIELD OF THE INVENTION

This invention relates implantable medical devices and more particularly to implantable medical device for cardiac pacing.

BACKGROUND OF THE INVENTION

While a variety of pacing modes are available, dual chamber pacing/sensing (DDD) is commonly utilized. With a DDD mode, atrial and ventricular events are both sensed. If an expected intrinsic event is not sensed within a predetermined time window, an appropriate atrial or ventricular pacing stimulus is delivered. This mode provides a great deal of control over the patient's cardiac rhythm and the timing (e.g., the atrial-ventricular or AV delay) may be modified based upon many different factors. One of the many benefits provided by the DDD mode is the ability to maintain AV synchrony. That is, for any given atrial event there will be a corresponding ventricular event, either intrinsic or paced.

Another beneficial feature is rate responsive (RR) pacing. With rate responsive pacing, a demand sensor is provided that seeks to approximate activity levels or physiological need from the patient and increase or decrease the pacing rate accordingly. For example, an accelerometer is used to sense the patient's motion. As the patient is more active, the accelerometer senses increased movement. This is recognized by the implantable medical device (IMD), which could be, for example, an implantable pulse generator (IPG) or implantable cardioverter defibrillator (ICD) with pacing capabilities, sometimes referred to as a PCD or pacemaker-cardioverter-defibrillator. In any event, the accelerometer's signal causes the IMD to pace at a higher rate. The assumption is that increased patient activity requires higher cardiac output and increasing the patient's heart rate (i.e., pacing rate) will lead to greater cardiac output. The higher the activity levels sensed, the higher the paced rate, up to a predetermined maximum rate. There are a variety of demand sensors the may be employed such as, a minute ventilation sensor, blood oxygen sensor, QT interval, chemical sensors, motion/movement sensors, or any other device that will approximate one or more demand parameters of the patient.

Typically, rate responsiveness is a positive feature that allows patients to engage in higher activity levels than would be possible with fixed rate pacing. The combination of DDD with rate response is also generally positive in that as the pacing rate is increased, the DDD mode will adjust parameters to assure proper timing throughout the cardiac cycle.

Recently, there has been a recognition that conducted or intrinsic ventricular depolarizations are vastly preferable to ventricular pacing in general and pacing in the right ventricular apex in particular. The difficulty in facilitating this preference is that in a great many patients, the intrinsic AV delay is so long that traditional DDD timing will almost always deliver a ventricular pacing pulse. In order to minimize or greatly reduce ventricular pacing, a protocol had been provided that, in one embodiment, utilizes an atrial based timing mode that allows a full cardiac cycle to elapse without ventricular activity; thus providing the greatest opportunity to safely allow intrinsic conduction whenever possible. These protocols are described in U.S. Ser. No. 10/755,454, filed Jan. 12, 2004, entitled "Preferred ADI/R: A Permanent Pacing Mode to Eliminate Ventricular Pacing While Maintaining Backup Support", which is a continuation of U.S. Ser. No. 10/246,816, filed Sep. 17, 2002, entitled "Preferred ADI/R: A Permanent Pacing Mode to Eliminate Ventricular Pacing While Maintaining Backup Support", which is a continuation-in-part of U.S. Ser. No. 09/746,571, filed Dec. 21, 2000, entitled "Preferred ADI/R: A Permanent Pacing Mode to Eliminate Ventricular Pacing While Maintaining Backup Support", recently granted as U.S. Pat. No. 6,772,005, all of which are herein incorporated by reference in their entireties.

As used herein, an atrial based pacing mode is a mode that is programmed to pace in the atria, but only to sense in the ventricles. True single chamber atrial pacing would imply that only a single lead is present and ventricular activity may not be sensed from within the ventricle nor would ventricular pacing be deliverable. In the present context we discuss an IMD operating in an atrial based mode (e.g., AAI, AAIR, ADI, ADIR), but at least having ventricular sensing capabilities. Though not required, such a device would generally include ventricular pacing. However, in order to deliver ventricular pacing the device would typically mode switch to a different mode, such as DDD, DDDR, DDI, or DDIR.

SUMMARY OF THE INVENTION

The present invention provides a method that includes operating an implantable medical device with a Ventricular Pacing Protocol (VPP) that selectively operates in an atrial based pacing mode and a dual chamber pacing mode. The method further includes performing a conduction check to determine if intrinsic conduction is present and if so, operating in the atrial based pacing mode, recording an indication each time a conduction check is performed to provide a count total equating to the number of conduction checks performed within a given time period, and monitoring a number of cardiac cycles operated in the atrial based pacing mode subsequent to each conduction check. The method also includes calculating an efficiency value equal to the number of cardiac cycles operated in the atrial based pacing mode during the given time period divided by the count total.

In one embodiment, the atrial based pacing mode is ADIR and the dual chamber mode is DDDR. In another embodiment, the atrial based pacing mode is AAI and the dual chamber mode is DDD.

Alternatively, the method further includes evaluating the efficiency value and increasing a frequency of the conduction checks if the efficiency value is above a first threshold. The method further includes decreasing the frequency of the conduction checks if the efficiency value is below a second threshold and maintaining the frequency of the conduction checks at a current level if the efficiency value is between the first and the second threshold.

In one embodiment, the conduction check includes operating for one cardiac cycle in the atrial based pacing mode. The method further includes, in one example, operating in the dual chamber pacing mode in a cardiac cycle immediately subsequent to the one cardiac cycle if no intrinsic ventricular activity is sensed during the one cardiac cycle. In another example, the method includes displaying the efficiency value on a medical device programmer.

In one embodiment, the VPP includes a mild level wherein 1:1 atrial-ventricular (AV) synchrony is maintained with an AV interval greater than an AV interval of the dual chamber pacing mode, a moderate level wherein an absence of ventricular activity in a given cardiac cycle is tolerated in the atrial based mode up to a first frequency of occurrence, and aggressive level wherein an absence of ventricular activity in a given cardiac cycle is tolerated in the atrial based mode up to a second frequency of occurrence, wherein the second frequency of occurrence is greater than the first frequency of occurrence.

In one example, the method includes changing the VPP from the aggressive level to the moderate level if the efficiency value is below a first predetermined threshold and changing the VPP from the aggressive level or the moderate level to the mild level if the VPP is below a second predetermined threshold. In one embodiment, the first and second predetermined thresholds are correlated to a patient's health status. In another embodiment, the patient's health status includes an indication for heart failure and a severity of heart failure. In another embodiment, heart failure severity is inversely correlated to the first and second predetermined values.

In one example, the present invention is a method that includes operating an implantable medical device with a Ventricular Pacing Protocol (VPP) that selectively operates in an atrial based pacing mode, a first dual chamber pacing mode having a first maximum AV interval of a first duration, and a second dual chamber pacing mode having a second maximum AV interval of a second duration that is greater than the first duration. The method also includes performing a conduction check to determine if intrinsic conduction is present and if so, operating in the second dual chamber pacing mode and recording an indication each time a conduction check is performed to provide a count total equating to the number of conduction checks performed within a given time period. The method further includes monitoring a number of cardiac cycles operated in the second dual chamber pacing mode subsequent to each conduction check and calculating an efficiency value equal to the number of cardiac cycles operated in second dual chamber pacing mode during the given time period divided by the count total.

The method may also include evaluating the efficiency value, increasing a frequency of the conduction checks if the efficiency value is above a first threshold, and decreasing the frequency of the conduction checks if the efficiency value is below a second threshold. The method further includes maintaining the frequency of the conduction checks at a current level if the efficiency value is between the first and the second threshold.

In one embodiment, the method includes increasing the AV interval from the first duration to the second duration. Alternatively, the conduction check includes incrementally increasing the AV interval from the first duration to the second duration. The method may further include displaying the efficiency value on a medical device programmer.

In one example, the VPP includes a mild level wherein 1:1 atrial-ventricular (AV) synchrony is maintained with an AV interval of the second duration, a moderate level wherein an absence of ventricular activity in a given cardiac cycle is tolerated in the atrial based mode up to a first frequency of occurrence, and aggressive level wherein an absence of ventricular activity in a given cardiac cycle is tolerated in the atrial based mode up to a second frequency of occurrence, wherein the second frequency of occurrence is greater than the first frequency of occurrence. In one embodiment, the second AV interval is reduced in duration if the efficiency is below a first predetermined value. Alternatively, the method includes changing from the second dual chamber mode to the first dual chamber mode if the efficiency value is below a predetermined value.

BRIEF DESCRIPTION OF THE DRAWINGS

FIG. 10 is a flowchart illustrating a process for VPP response to intrinsic AV delay parameters.

DETAILED DESCRIPTION OF THE PREFERRED EMBODIMENTS

Figure 1:
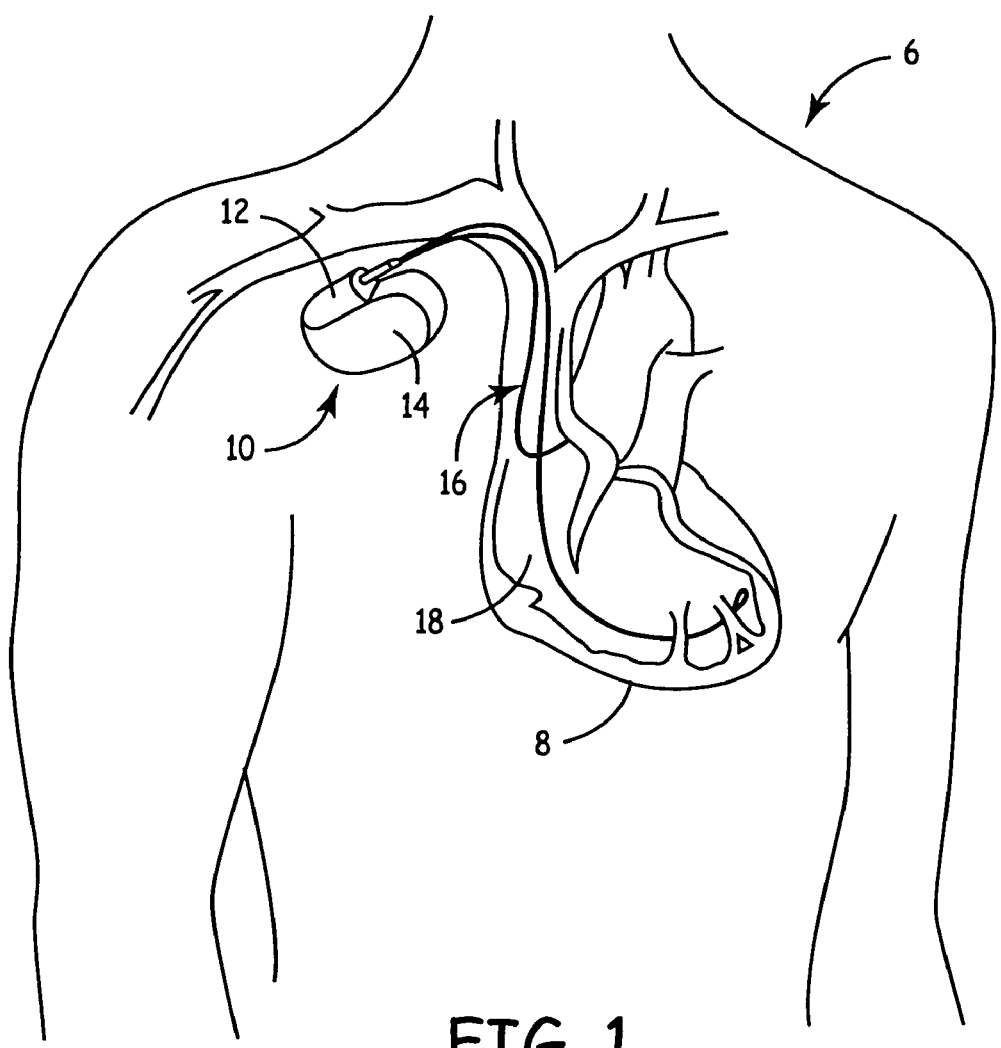
FIG. 1 illustrates an implantable medical device system in accordance with an embodiment of the invention implanted in a human body.

FIG. 1 is a simplified schematic view of one embodiment of implantable medical device ("IMD") 10 of the present invention implanted within a human body 6. IMD 10 comprises hermetically sealed enclosure 14 and connector module 12 for coupling IMD 10 to pacing and sensing leads 16 and 18 within heart 8.

Figure 2:
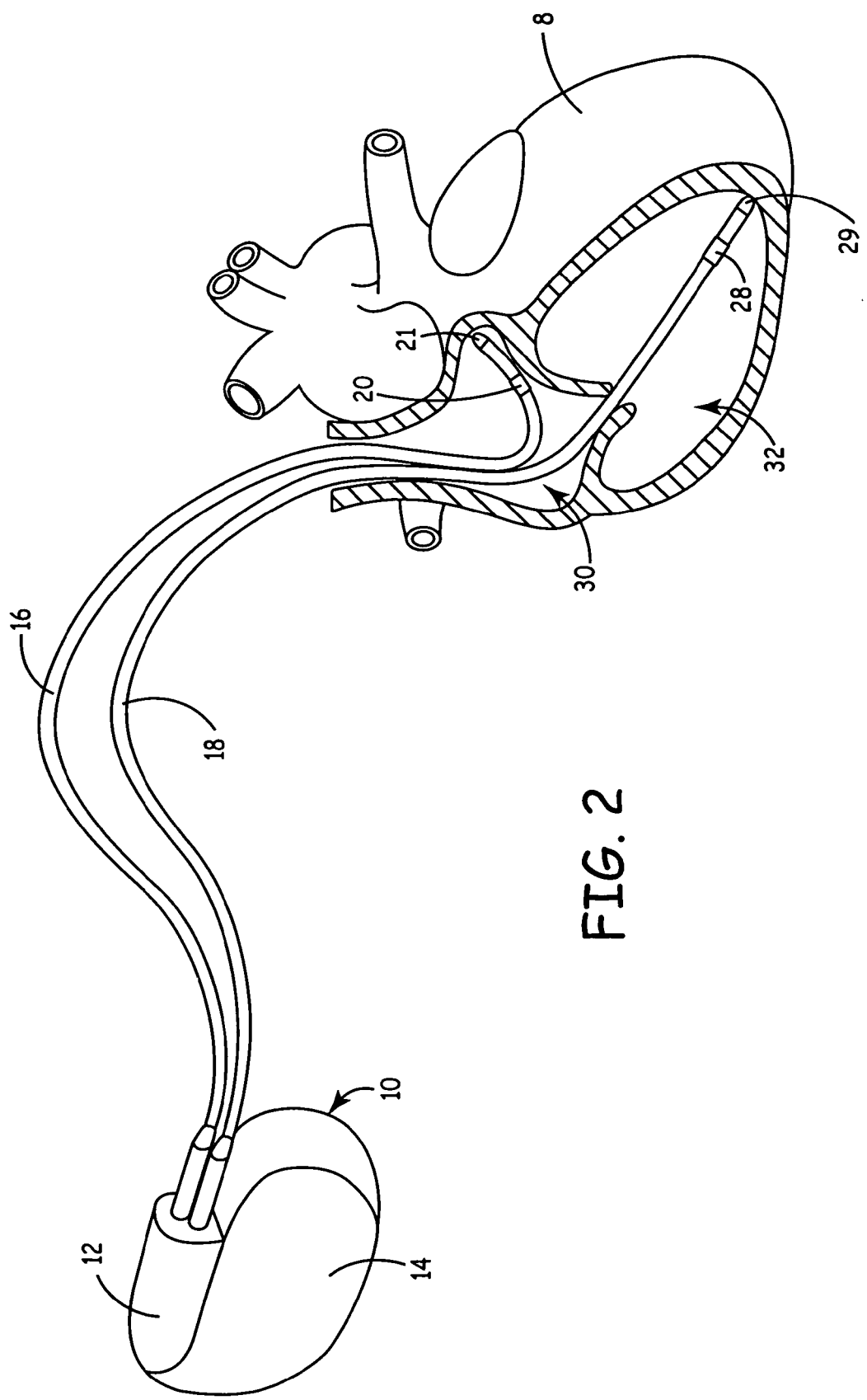
FIG. 2 illustrates one embodiment of an implantable pacemaker device system in accordance with the present invention coupled to a human heart.

FIG. 2 shows atrial and ventricular pacing leads 16 and 18 extending from connector module 12 to the right atrium 30 and right ventricle 32, respectively, of heart 8. Atrial electrodes 20 and 21 disposed at the distal end of atrial pacing lead 16 are located in the right atrium 30. Ventricular electrodes 28 and 29 at the distal end of ventricular pacing lead 18 are located in the right ventricle 32.

Figure 3:
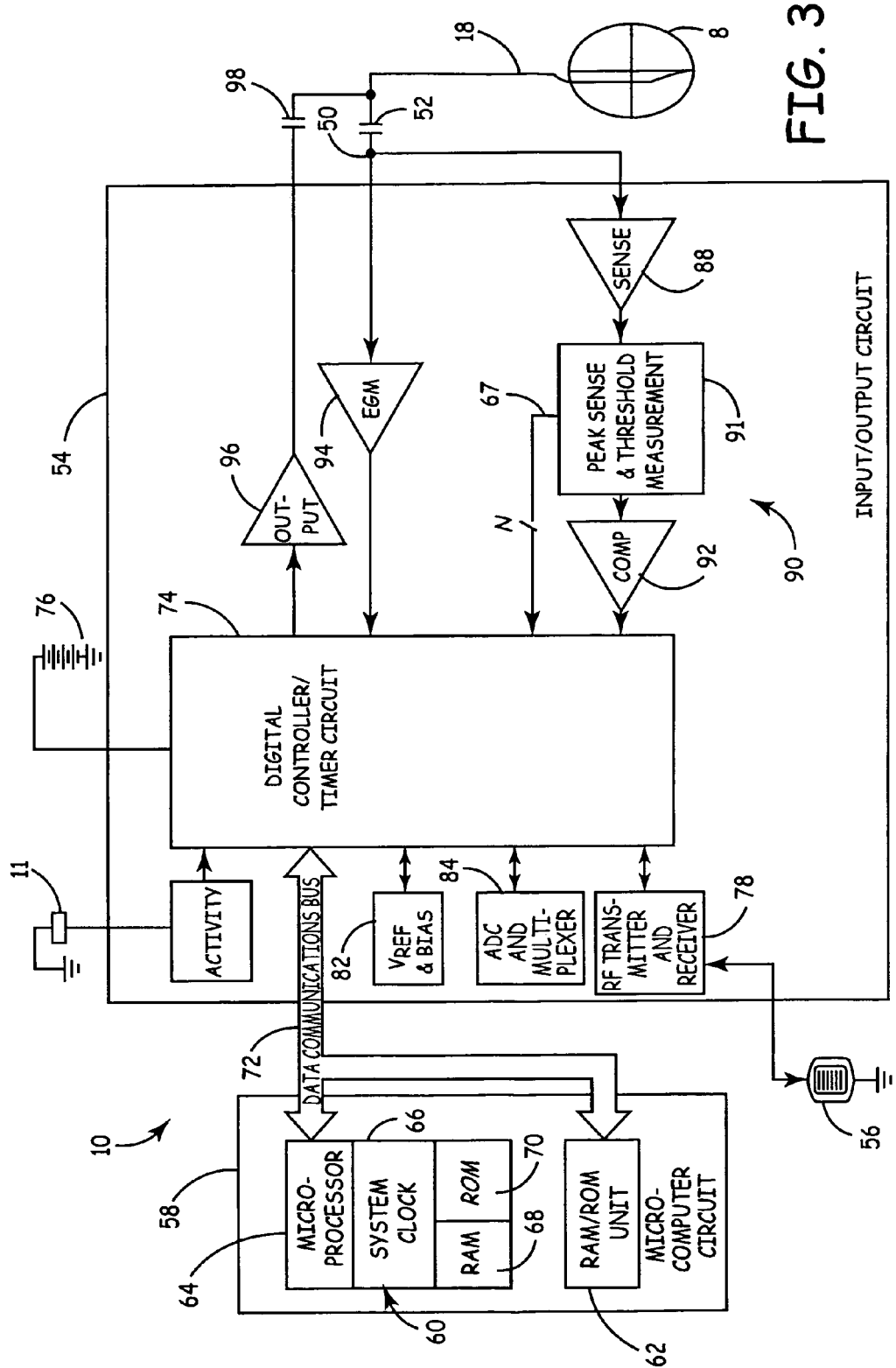
FIG. 3 is a block diagram illustrating the various components of one embodiment of an implantable pacemaker device configured to operate in accordance with the present invention.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is programmable by means of an external programming unit (not shown in the figures). One such programmer is the commercially available Medtronic/Vitatron Model 9790 programmer, which is microprocessor-based and provides a series of encoded signals to IMD 10, typically through telemetry via radio-frequency (RF) encoded signals or inductive coupling As shown in FIG. 3, lead 18 is coupled to node 50 in IMD 10 through input capacitor 52. Activity sensor or accelerometer 11 is attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. Software-implemented algorithms stored in microcomputer circuit 58 control the pacing rate.

Microcomputer circuit 58 comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the figures. Antenna 56 is connected to input/output circuit 54 to permit uplink/downlink telemetry through RF transmitter and receiver telemetry unit 78.

As further shown in FIG. 3, VREF and Bias circuit 82 generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish an overall escape interval of the IMD 10 as well as various refractory, blanking and other timing windows for controlling the operation of peripheral components disposed within input/output circuit 54.

Figure 4:
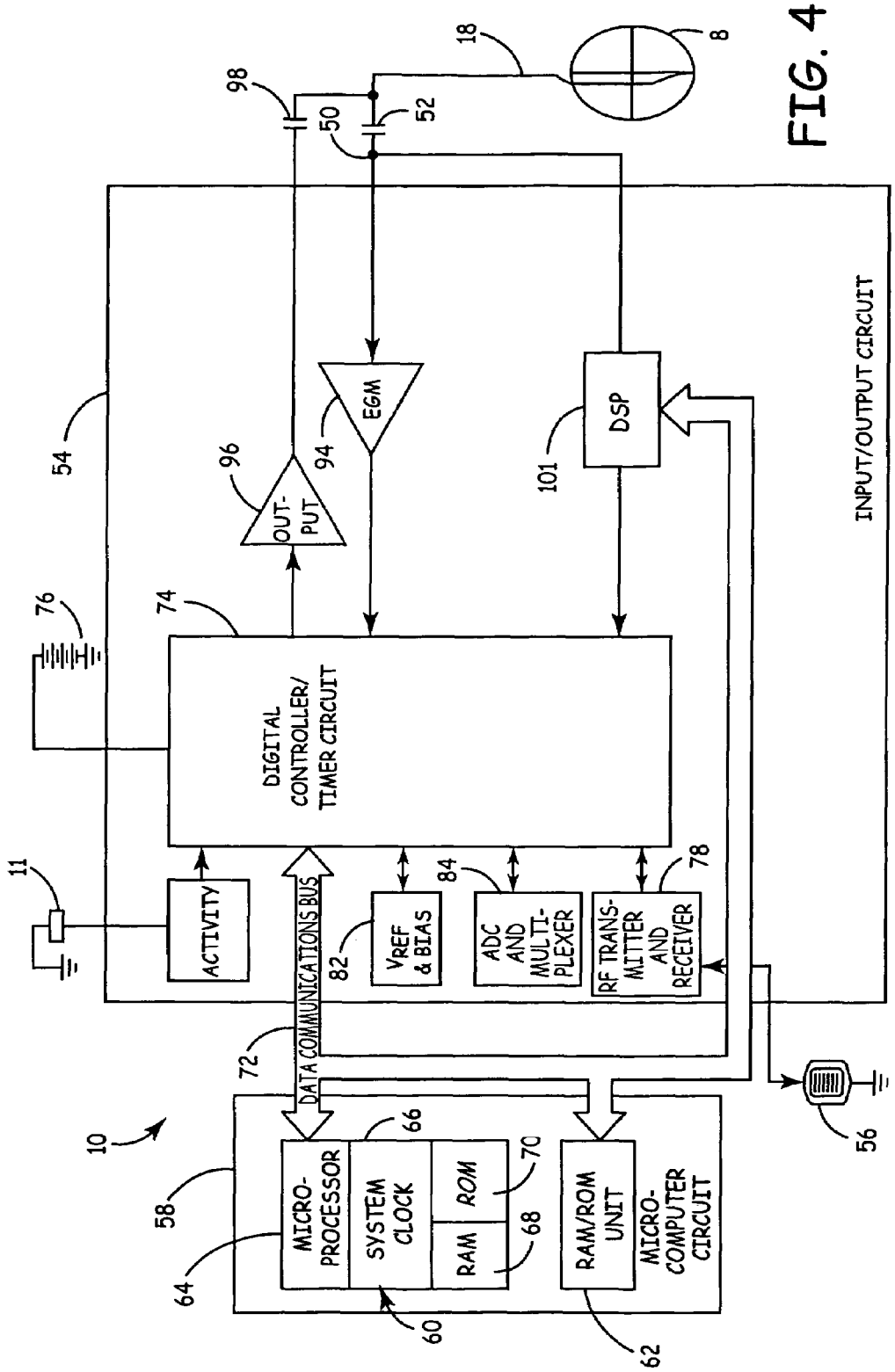
FIG. 4 is a block diagram illustrating the various components of another embodiment of an implantable pacemaker device configured to operate in accordance with the present invention.

Digital controller/timer circuit 74 is coupled to sensing circuitry 91, including sense amplifier 88, peak sense and threshold measurement unit 90 and comparator/threshold detector 92. The embodiment of FIG. 4 conforms substantially to that shown in FIG. 3, but incorporates a digital signal processor (DSP) 101 in lieu of sensing circuitry 90, including sense amplifier 88, peak sense and threshold measurement unit 91, and comparator/threshold detector 92. DSP 101 receives signals, which may be amplified and processed, from lead 18. DSP 101 digitizes the signals for analysis. DSP 101 may be coupled to micro-computer circuit 58 via data communications bus 72, permitting the microcomputer circuit to modify the processing characteristics of the DSP. Also, DSP 101 may provide signal data to microcomputer circuit 58 for added analysis or control functions. An example of an implantable medical device incorporating a DSP for ECG signal analysis is disclosed in U.S. Pat. No. 6,029,087 to Wohlgemuth, the entire content of which is incorporated herein by reference.

Digital controller/timer circuit 74 is further preferably coupled to electrogram (EGM) amplifier 94 for receiving amplified and processed signals sensed by lead 18. In the embodiment of FIG. 3, sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. Alternatively, similar signals can be generated by DSP 101 for transmission to digital controller/timer circuit 74. The electrogram signal provided by EGM amplifier 94 is employed when IMD 10 is being interrogated by an external programmer to transmit a representation of a cardiac analog electrogram.

Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art.

In some embodiments of the present invention, IMD 10 may operate in various non-rate-responsive modes, including, but not limited to, AAI, ADI, DDD, DDI, VVI, VOO and VVT modes. In other embodiments of the present invention, IMD 10 may operate in various rate-responsive modes, including, but not limited to, ADIR, AAIR, DDDR, DDIR, VVIR, VOOR and VVTR modes. Some embodiments of the present invention are capable of operating in both non-rate-responsive and rate responsive modes IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 5A:
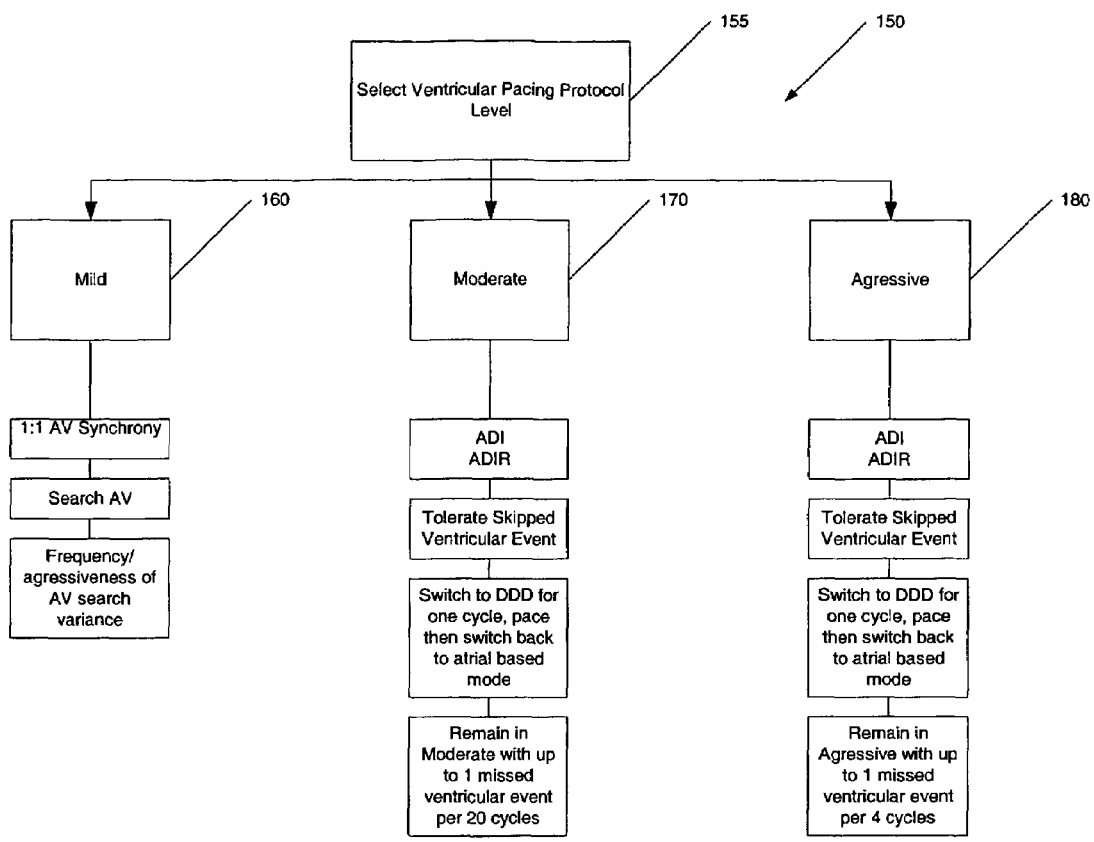
FIG. 5A is a block diagram illustrating a Ventricular Pacing Protocol.

FIG. 5A illustrates a Ventricular Pacing Protocol (VPP) (150) that provides programmable or selectable settings for the IMD 10 that reduce or minimize ventricular pacing to varying degrees. The IMD 10 is operable in a traditional mode (e.g., DDD, DDDR, etc.). When VPP is enabled, the physician will select the VPP having the desired level (155) of aggressiveness. As will be described, the IMD 10 may move from a given VPP level to a less aggressive VPP level, may switch back to the more aggressive VPP level, or may switch out of VPP, but will generally not engage a VPP level higher (in aggressiveness) than selected by the programming physician. For example, in one embodiment more aggressive VPP levels are tolerated by a given patient during sleep; thus, the IMD 10 adjusts to this level based on a sensor indication of sleep and/or a time selection (e.g., nocturnal hours). The VPP levels are described for illustrative purposes only and it should be appreciated that more or fewer levels could be provided consistent with the present invention. Furthermore, relative terms are used to describe the VPP levels for illustrative purposes only and are non-limiting. The examples provided herein will indicate for consistency that "higher" levels are "more" aggressive than "lower" levels of VPP. Aggressiveness relates to the tolerance that the VPP will have for missed or delayed ventricular events.

The least aggressive VPP setting in this embodiment is the mild VPP (160). Mild VPP functions similarly to DDD or DDDR in that AV synchrony is maintained. This is, mild VPP (160) will normally deliver a ventricular pacing pulse in every cardiac cycle unless certain intrinsic ventricular activity is sensed. In order to do so, an AV delay is provided. At the end of the AV delay, the ventricular pacing pulse is delivered absent appropriate intrinsic ventricular activity. In order to promote intrinsic ventricular depolarization, the AV interval in the mild VPP can be rather long, e.g., 350-500 ms, as compared to standard settings in DDD or DDDR. Thus, for a patient with intact but prolonged intrinsic AV conduction, the longer AV interval will permit intrinsic ventricular depolarization. If no intrinsic conduction occurs, the AV interval is shortened to achieve hemodynamic optimization. Periodically, a search is conducted by lengthening the AV delay to determine if AV conduction has returned. The frequency of conducting such a search and the length of the AV interval are variables that the IMD 10 or the programming physician can change, either manually or automatically by the IMD 10 depending upon the rate of success. The search may be realized by extending the AV delay for a single beat or for more beats and the extension may become active entirely at once or will gradually be achieved over several beats. In addition, when pacing occurs at the end of the extended AV delay, either as a result of a failed scan or after a period of intrinsic AV conduction when the AV conduction fails, this may occur for one or for more cardiac cycles before returning to the shorter value for more optimized hemodynamics.

In the moderate VPP setting (170), the IMD 10 operates in an atrial based pacing mode, such as AAI, ADI, AAIR, ADIR or the like. For any given cycle in the atrial based pacing mode, ventricular depolarization will only occur if it is intrinsic. That is, no ventricular pacing pulse will be delivered. If a cycle occurs without a ventricular event, the IMD 10 then mode switches to DDD, DDI, DDDR, or DDIR for the next cardiac cycle. For simplicity, these traditional modes will be collectively referred to as dual chamber pacing modes. It should be appreciated that a reference herein to any specific mode such as DDDR, is meant to be illustrative and any of the traditional dual chamber pacing modes may be interchanged as appropriate.

In the cycle subsequent to the one devoid of a ventricular event, the IMD 10 will operate in DDD and deliver a ventricular pace (unless precluded by intrinsic activity as is standard in the DDD modality). For the next subsequent cycle (or after a certain number of beats or period of time in the dual chamber modality, in certain embodiments), the IMD 10 mode switches back to the atrial based pacing mode. This activity is all part of the moderate VPP (170); that is, these mode switches are part of the protocol not a departure from the protocol.

Another aspect of the VPP is that it monitors the number of missed ventricular events. If more than a predetermined number of missed ventricular events occur within a specified period or within a specified number of beats, then the IMD 10 mode switches to DDD and remains in DDD for a prolonged period of time. Periodically, the VPP will initiate a conduction check by mode switching to the atrial based pacing mode for one cycle to determine if intrinsic conduction has returned. If it has, the process operates as previously described. If not, the IMD 10 mode switches to DDD and again remains there until the next conduction check. If intrinsic activity occurs and precludes a ventricular pace during DDD, the VPP, in one embodiment, will cause the IMD 10 to switch to the atrial based pacing mode.

In the moderate VPP (170), the protocol will tolerate up to one missed ventricular event in twenty consecutive cardiac cycles. In the aggressive VPP 180, the protocol will tolerate up to one missed ventricular event in four consecutive cardiac cycles. When these parameters are exceeded, the IMD 10 mode switches to DDD for a prolonged period of time, as previously explained. These numerical embodiments are merely illustrative examples and are not limiting. That is, for a given number of cardiac cycles, the more cycles tolerated without ventricular activity, the more aggressive the protocol is labeled. The particular number chosen may be selected for any number reasons and those provided above are merely exemplary. Similarly, more "levels" of aggressiveness may be defined by simply providing more selectable tolerance values. Finally, rather than designating levels, the VPP aggressiveness may be added as a programming parameter with the particular number of cycles tolerated numerically selectable.

Figure 5B:
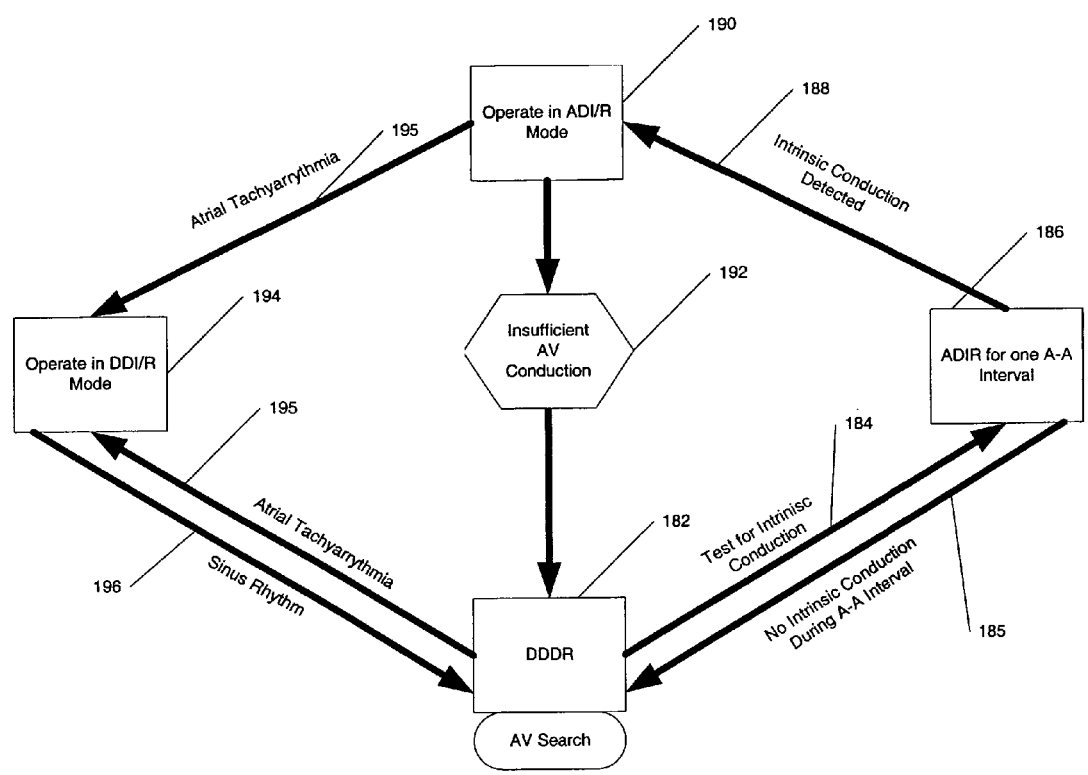
FIG. 5B is a block diagram illustrating a Ventricular Pacing Protocol.

FIG. 5B is a block diagram that illustrates operation of the IMD 10 in a VPP. For illustrative purposes, the IMD 10 is described as initially operating in the DDDR (182) mode. At some point in time, as defined by the VPP, and as early as the first cardiac cycle operated under the VPP the IMD 10 will perform a conduction check. The type of conduction check performed will depend upon the level of aggressiveness of the VPP and in general depends upon whether the VPP is capable of mode switching to an atrial-based mode. Assuming a mode switch to the atrial-based mode (ADIR as used in this example), the IMD 10 will mode switch to and operate in ADIR (186) for one complete cardiac cycle. If intrinsic ventricular depolarization is not sensed, then the IMD 10 will mode switch (185) back to the dual chamber mode or in this embodiment, DDDR. If intrinsic ventricular depolarization is sensed, then the IMD 10 operates (190) in the atrial-based pacing mode. As described above, the varying levels of aggressiveness determine what constitutes sufficient AV conduction to allow the IMD 10 to remain in the atrial based pacing mode. If, according the VPP parameters, there is insufficient intrinsic conduction (192), then the IMD 10 will mode switch to and operate in DDDR (182). This is distinct from the iterative returns to a dual chamber mode to provide ventricular pacing after a cardiac cycle devoid of a ventricular depolarization with a predetermined return to the atrial based mode in a subsequent cycle.

Whether in the DDDR mode or in ADIR mode, the IMD 10 will mode switch to DDIR (194) in the event that an atrial tachyarrhythmia (195) is sensed. When a normal sinus rhythm (196) is restored, the IMD 10 will mode switch to the DDDR mode and proceed accordingly.

When the VPP is programmed to a mild level of aggressiveness, and use of the atrial based pacing mode is not permitted, then the IMD 10 will operate in the DDDR mode. The IMD 10 utilizes the AV search function to identify and promote intrinsic conduction, as described above.

Figure 5C:
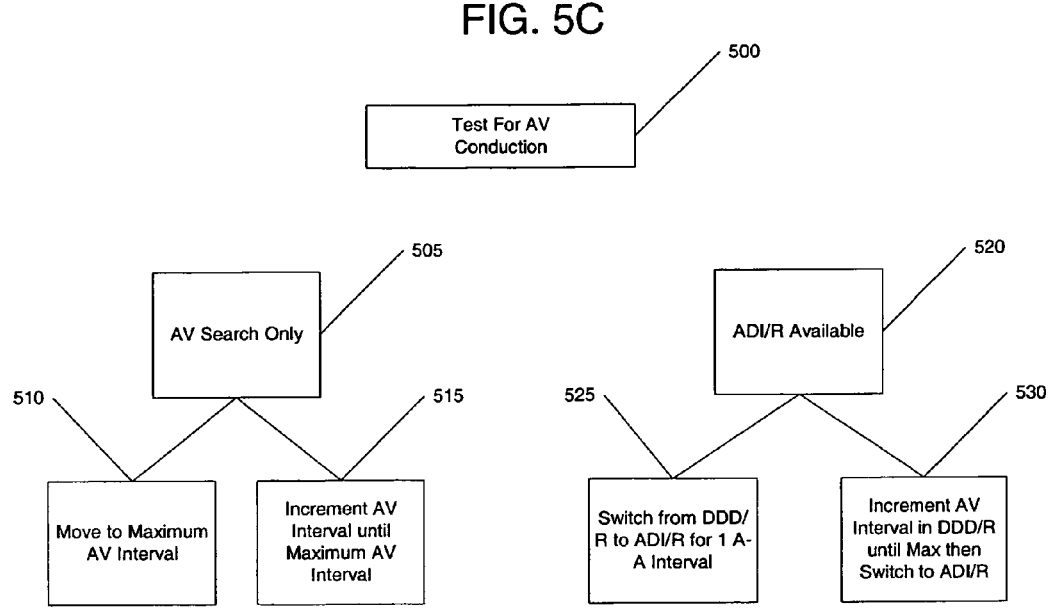
FIG. 5C is a block diagram illustrating conduction check parameters for a Ventricular Pacing Protocol.

FIG. 5C is a block diagram that illustrates various tests available in the VPP to determine whether intrinsic AV conduction is present. When the VPP will only permit an AV search (505), then the IMD 10 will periodically extend the duration of the programmed AV interval. While the numerical value may vary depending upon the parameters of the VPP, there will be some maximum permissible AV interval that the IMD 10 can utilize. Thus, one conduction test permits the IMD 10 to set the AV interval to this maximum value (510). For any given cardiac cycle, use of this maximum value will provide the highest level of promotion for intrinsic conduction in the mild VPP.

When performing such a conduction check, intrinsic conduction might not immediately return as the cardiac tissue and conduction pathway might take a period of time to normalize in a particular patient. Where this may be of concern, the VPP provides intrinsic conduction promotion parameters that may be selected. Thus, when conducting an AV search by extending the interval to the maximum duration (510), a failure to sense intrinsic conduction in the first cardiac cycle will not terminate the test. That is, the VPP maintains the maximum interval for some predetermined number of cardiac cycles to provide an opportunity for intrinsic conduction to return. The number of cycles permitted may be standardized, adjusted based upon patient specific data, or programmed by a clinician. Of course, in this embodiment, if intrinsic conduction fails to return for a given cycle then the IMD 10 provides a ventricular pace at the termination of the extended AV interval. If no intrinsic conduction is sensed after the permitted number of cycles, the AV interval is returned to the shorter duration.

Another intrinsic conduction promotion parameter is to increment (515) the AV interval, rather than immediately extending the interval to its maximum value. For example, the "standard" DDD AV interval may be 150 ms for a given patient. For the first increment, the AV interval is extended to e.g., 200 ms, then 250 ms, etc. up until the maximum value, e.g., 500 ms. Each increment may be a single cardiac cycle at each interval, a static predetermined number of cycles at each AV interval, or a dynamic number of cycles at each interval. Whichever methodology is employed, if intrinsic AV conduction is sensed, the AV interval is maintained at that or a longer setting until a loss of intrinsic conduction occurs sufficient to trigger the VPP to provide the shorter AV interval.

The IMD 10 may utilize a VPP that permits operation in an atrial based pacing mode (520). When a test is performed to check for intrinsic conduction, the VPP mode switches the IMD 10 to the atrial based pacing mode, e.g., ADIR, for one cycle; thus, the heart is given the complete cardiac cycle to facilitate intrinsic conduction. If during any point of that cardiac cycle, intrinsic conduction occurs, then the IMD 10 determines that it can operate in the atrial based pacing mode, as described.

As indicted above, intrinsic conduction in the cardiac tissue or conduction pathway may, in some cases, take some time to return to its fullest potential. Thus, another intrinsic conduction promotion parameter is to incrementally extend the AV interval before operating for a full cycle (530) in the atrial based pacing mode. For example, the IMD 10 increases the AV interval from its normal setting to e.g., 200 ms; in a subsequent cycle 250 ms; in subsequent cycle 300 ms; eventually providing an AV interval of 500 ms. Then, the IMD 10 mode switches to the atrial paced pacing mode for one complete A-A interval. In this manner, the underlying or intrinsic conduction is given a greater period of time (over several cycles) to present itself absent rigorous ventricular pacing with short AV interval. Of course, intrinsic conduction may be sensed during any of these cycles and if so, the IMD 10 will mode switch to the atrial based pacing mode. That is, the conduction test need not move through the entire sequence and include a test cycle in the atrial base mode. Intrinsic conduction in any cycle is considered a positive result and lead to a mode switch to the atrial based mode.

In another embodiment, incrementally stepping through AV intervals of progressively longer length still requires a testing cycle in the atrial-based mode. When intrinsic conduction is sensed, the testing process may complete subsequent AV interval extensions and then operate in the atrial-based mode for one A-A interval. Alternatively, the testing process may bypass subsequent AV interval extensions and switch to the atrial based pacing mode for a test cycle upon sensing intrinsic conduction during the extended AV interval.

This distinction between requiring the test cycle in the atrial based pacing mode or mode switching into the atrial based pacing mode based upon sensed intrinsic conduction during an AV interval relates to the effect that a subsequent cycle, lacking intrinsic conduction will have on the IMD 10. That is, in an ADIR test cycle, a lack of conduction will result in a mode switch to and continued operation in DDDR for some period of time. If however, the VPP is operating ADIR, multiple cardiac cycles will have to be devoid of intrinsic conduction to cause the VPP to mode switch to DDDR for an extended period of time.

For example, the aggressive VPP tolerates an absence of intrinsic conduction in one out of four cycles. Thus, in such an example, if intrinsic conduction was anomalously detected during a test cycle, the first cycle of operation in ADIR will be devoid of intrinsic conduction. In the subsequent cycle, the IMD 10 operates in DDDR and a ventricular pace is delivered. In the next subsequent cycle, the IMD 10 operates again in ADIR and is devoid of intrinsic conduction. Now, two of three and hence two of four consecutive cardiac cycles lack intrinsic conduction and the VPP will mode switch to DDDR for an extended period of time.

During periods of exercise, particularly strenuous exercise, there is a constant and high demand for cardiac output. Naturally, the atrial rate will increase to provide that increased cardiac output. This may occur intrinsically; that is, the SA node will pace the heart at an appropriately elevated rate in response to various factors of, e.g., the autonomic nervous system. Alternatively, the IMD 10 may utilize an activity sensor or other physiological proxy sensor and determine that rate should be increased. In response, the atrial pacing rate is elevated appropriately and up to an upper rate limit.

In either case, the A-A interval becomes correspondingly shorter. In response, the AV node will normally decrease the intrinsic AV delay; thus, ventricular depolarization will occur temporally closer to the preceding atrial depolarization. With an IMD operating in DDDR, the AV and VA interval are appropriately controlled. In the VPPs discussed, intrinsic ventricular depolarization is preferred and in certain cardiac cycles ventricular pacing is essentially precluded.

For various reasons, the intrinsic AV delay for a given patient may not decrease appropriately or may actually increase in response to an elevation in the atrial rate. Alternatively, or in addition thereto, various degrees of conduction block may occur during this period either statistically by chance or as a result of the increase in activity, rate, or a related parameter. In these cases, while operating under certain of the VPPs, a cardiac cycle may be devoid of ventricular depolarization. This results in an elongated R-R interval covering the missed beat(s). As indicated, this is normally non-symptomatic during periods or rest and normal activity. In the more aggressive VPP levels, a higher number of missed ventricular events is permitted. This could lead to a cycle of missed events that is tolerated by the protocol but may be perceivable to the patient during strenuous exercise. For example, if every fifth cycle were devoid of ventricular activity, the aggressive VPP, in one embodiment, would continue.

Figure 6:
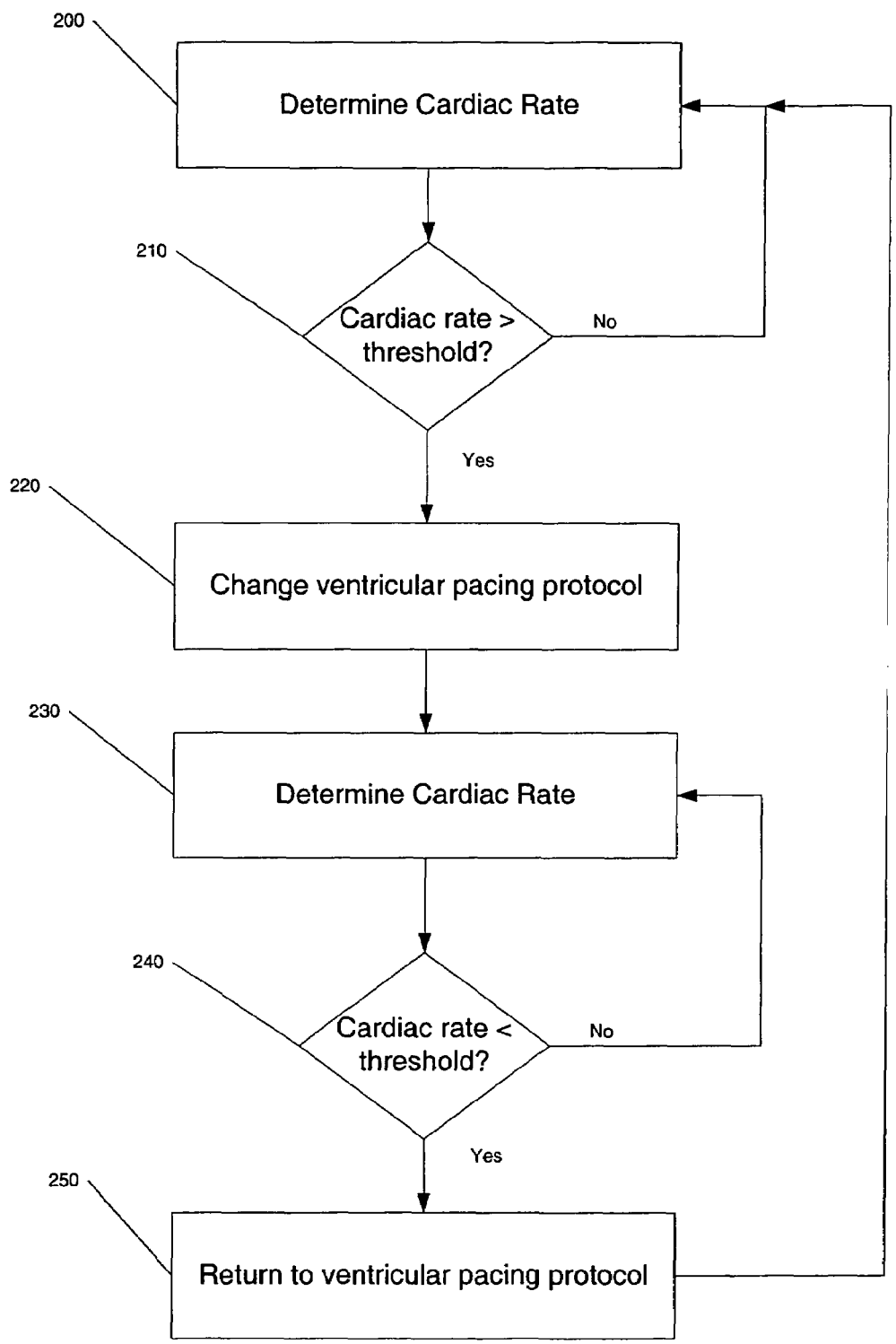
FIG. 6 is a flowchart illustrating a process for managing the Ventricular Pacing Protocol based on physiological rate.

FIG. 6 is a flowchart illustrating a process to address the effects that an elevated heart rate may have with one of the ventricular pacing protocols. While operating in one of the VPPs, the IMD 10 monitors (200) the cardiac rate. The cardiac rate as used herein includes either the intrinsic rate or the sensor driven or device determined rate based upon programming values or activity levels. Typically, this refers to the atrial rate, either paced or sensed; however, sensing the ventricular rate or other cardiac timing parameters could also be utilized to determine the cardiac rate. While decisions could be based upon individual measurements, i.e., rate as calculated by an A-A timing interval, the determined (200) rate is generally based upon a running average over a predetermined number of cardiac cycles. The predetermined number of cycles is selected large enough such that anomalous rate variations do not over-affect the process and low enough that the IMD 10 responds quickly enough to actual sustained increases in cardiac rate. While not limited as such, the predetermined number of cycles may be on the order of 5, 10, 20, or more cycles.

Alternatively, the averaged rate may be based upon the physiological rate as defined and utilized in various Medtronic Vitatron products. In summary, the physiologic rate is a tracking rate that varies on a beat-to-beat basis with, e.g., the atrial rate. As variance in the tracked rate occurs, the physiologic rate only varies by a set numerical value (e.g., 2 bpm) in the direction indicated. For example, if the tracked rate drops by 10 bpm (based on a given A-A or V-V interval), the physiologic rate is dropped by 2 bpm. One the next cycle, the physiologic rate can move another 2 bpm and so on. Thus, large beat-to-beat variances are not immediately reflected in the physiologic rate and this provides a smoother value to utilize. There is a limit to the amount of change that is not tracked. For example, if at any time the physiologic rate varies from the tracked rate by greater than, e.g., 15 bpm then this is determined to be a classified event and processed as such. A classified event would be, for example, an indication of the onset of tachycardia. As used herein, the cardiac rate would include a value determined either based upon a beat to beat value, by averaging over a given number of cycles, by utilizing a physiologic rate algorithm, or by some other smoothing function.

As the cardiac rate is determined (200), that rate is compared (210) with a threshold value. The threshold value is meant to delineate rest or normal activity levels from elevated activity such as exercise and particularly strenuous exercise. In one embodiment, the threshold value is 95 bpm. Depending upon the patient or physician concerns, the threshold value may be selected from any value between the upper and lower rate limits. That is, certain patients may be more or less tolerant of these affects at varying rates and the threshold can be set accordingly. Younger patients implanted with an IMD 10 may have upper rate limits on the order of 190 bpm; thus, their threshold might be higher than, for example an elderly patient. Rather inactive patients may be strenuously exerting themselves at 75 bpm. Thus, the threshold will be determined for a patient and may be varied as the patient's condition changes. In general, the threshold will be between 75 bpm and 120 bpm, and typically between 85 bpm and 100 bpm.

As an alternative to setting a fixed threshold value, the threshold value could be programmed to be the lower rate limit (LRL) plus some fixed constant; the LRL plus a variable dependant upon certain factors (age, condition, activity, previous rate trends, etc.), the upper rate limit (URL) minus some fixed constant, or the URL minus a variable dependant upon certain factors (age, condition, activity, previous rate trends, etc.). Thus, the threshold value will change in response to other programming or mode variations such as changes to the upper or lower rate limits.

If the cardiac rate is at or below the threshold, then the IMD 10 continues to monitor the rate (200) and will continue to operate according to the VPP. If however, the cardiac rate exceeds the threshold (210), then the ventricular pacing protocol is changed (220).

How the VPP is changed will depend upon which VPP is in place when the cardiac rate exceeded the threshold. In general, the issues presented above are of concern when more aggressive protocols are in place; that is, an entire cycle may pass without ventricular activity. It is from these protocols that a change would be made.

One change (220) is to switch from the current VPP to another appropriate (non-VPP) pacing mode, such as DDDR. Alternatively, the change (220) would be switching to a less aggressive VPP or switching to a VPP that would ensure 1:1 AV synchrony at a hemodynamically optimal setting. That is, intrinsic ventricular depolarization is still preferred and promoted to the extent possible; however, ventricular pacing will be delivered to assure each cardiac cycle includes ventricular depolarization and that there is a sufficient VA interval based upon the cardiac rate.

Figure 7:
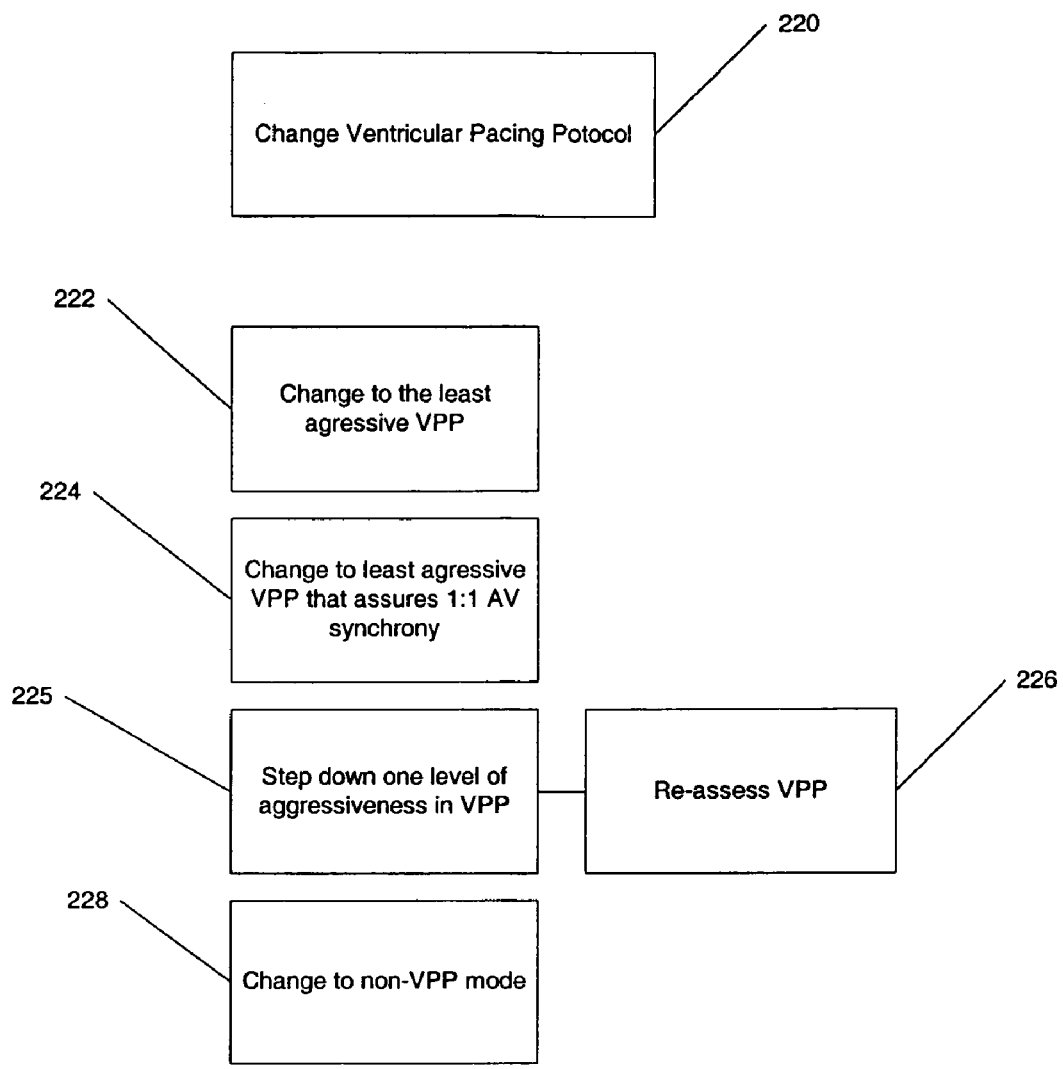
FIG. 7 is a block diagram illustrating various change options for the Ventricular Pacing Protocol.

FIG. 7 illustrates examples of changes to the VPP that may be made (220). When changing the VPP at (220), the IMD 10 will move (222) from the current VPP employed to the least aggressive VPP available (e.g., Mild 160, FIG. 5A). When more levels are provided that assure 1:1 AV synchrony, then the change (210) could be to the least aggressive VPP that assures this (224), but not necessarily the least aggressive (overall) VPP. As another change option, the VPP could be stepped down by one (or any predetermined number) level of aggressiveness (225). Thus, if the VPP were operating the in aggressive VPP (180), then the IMD 10 would change to the moderate VPP (170). Likewise, if the IMD 10 were in the moderate VPP (170), the change would be to the mild VPP (160). In any of these embodiments, the changed VPP may be reevaluated (226) to determine if it is appropriate for the patient's cardiac rate. If additional changes are required, the VPP may again be changed as indicated herein. Another change (220) that could be made is to move out of the VPP into a non-VPP mode.

Referring again to FIG. 6, when the change (220) has been made, the IMD 10 continues to monitor (230) the cardiac rate. A determination is made (240) as to whether the averaged rate has returned to or fallen below the threshold. Assuming the rate is still above the threshold, the IMD 10 continues to operate in the mode or protocol that it was changed to at (220) and continues to monitor the averaged rate (230). When it is determined (240) that that averaged rate has returned to or fallen below the threshold, then the IMD 10 will return (250) to the ventricular pacing protocol in place prior to the elevation in cardiac rate.

Alternatively, though not separately shown, the threshold employed at (240) could be a different value than the threshold employed at (210) and/or the predetermined number of cycles utilized to determine the average rate could be set differently at (230) then at (200). That is, there may be a desire to assure a return to normal or resting activity levels prior to resuming the ventricular pacing protocol rather than simply a pause or temporary reduction during, e.g., a strenuous aerobic workout. This would simply be a matter of physician programming preference, as the present invention will appropriately address the situation if the cardiac rate varies about the threshold.

One mechanism to prevent repetitive transitions across the lower threshold is to require a return to a threshold (240) that is significantly lower than the upward threshold (210). For example, the lower threshold may be 10, 15, 20 or more beats per minute lower than the upper threshold. Another mechanism would be to require that the cardiac rate remain at or below the lower threshold (240) for a longer period of time before considering the rate to have returned below the threshold. That is, not simply a binary threshold crossing to make the determination. The duration may be based on a predetermined period of time (e.g., 10-60 seconds, 1-5 minutes, 5-10 minutes, etc.). In addition, a determination that the lower threshold has been crossed could require both the lowered threshold value and the duration requirement. In any event, a determination will eventually be made that the cardiac rate has returned to a value below the lower threshold value (240).

This return (250) to the prior ventricular pacing protocol is presumed to be an appropriate course of action. The patient is presumed to benefit from returning to the previously established level of aggressiveness with the VPP. Of course, for any number of reasons, the patient's condition may no longer tolerate that level of aggressiveness even though the cardiac rate has returned below threshold. For example, partial or complete conduction block could occur that would then require ventricular pacing. Thus, the return to the more aggressive VPP is handled like any other conduction check employed by these protocols. For example, the AV delay could be progressively elongated to search for intrinsic conduction, a switch may be made to ADIR for one complete cycle, or similar parameters would be employed to assure that there is underlying intrinsic conduction justifying the level of aggressiveness with the VPP.

It should be appreciated that one benefit of the VPPs is the reduction of ventricular pacing and the promotion of intrinsic conduction. During the course of strenuous exercise and the reduction of aggressiveness in the VPP, the patient could receive ventricular pacing that may have been excluded in a more aggressive mode; however, this will generally preclude missed ventricular events and longer R-R intervals. Furthermore, patients having the IMD 10 will typically only exercise for relatively short periods of time; thus, ventricular pacing is only minimally increased. For those patients who may exercise more frequently or who otherwise do not encounter such symptoms at increased cardiac rates, the VPP could be programmed to remain in effect, even above the threshold.

When employing one of the ventricular pacing protocols (VPP), a determination of effectiveness can be made based upon certain objective parameters. Effectiveness relates to how many paced ventricular events have been avoided.

As indicated, the more aggressive VPPs will tolerate a missed ventricular event for an entire cycle; pace in a subsequent cycle and return to an atrial based pacing mode for the next subsequent cycle. If the patient has developed complete conduction block and this pattern is continued, the effect is to only have ventricular depolarization in every other cycle. In other words, the ventricular rate is halved with respect to the atrial rate. Thus, for a patient with complete conduction block, ventricular pacing is greatly reduced, i.e., halved; however, this is generally not a hemodynamically sound pacing methodology, in and of itself. This halving effect illustrates that a measure of the effectiveness of a VPP does not rest solely with the number of ventricular pacing pulses averted.

Similarly, the number of mode switches or number of switches between various VPPs does not necessarily determine effectiveness. Rather, effectiveness is determined by the successful switch into a VPP, wherein success is defined by having a number of cardiac cycles with intrinsic AV conduction and intrinsic ventricular depolarization. As such, effectiveness is defined according to the present invention as:

$$\text{Effectiveness (E)} = N_{beats}/N_{switches}$$

where Nbeats=the number of cycles following a switch with intrinsic ventricular depolarizations and where Nswitches=the number of switches from the atrial based pacing mode to a ventricular pacing mode (e.g., DDD or DDDR)

Thus, the larger the value of E, the greater the effectiveness. As such, effectiveness is not simply the "gain" in the number of intrinsic ventricular depolarizations, nor is it simply the number of switches made. As an example, if over a given time period there were 100 switches made, and there were 10 beats with intrinsic conduction for each switch, then the patient has received 1000 less ventricular pacing pulses than might have occurred absent the VPP. If, over the same period of time, there were 10 switches made with 100 beats with intrinsic activity for each, the same 1000 ventricular paces have been avoided. However, according to the above formula the effectiveness is much greater in the later case.

Case 1: E=10/100=0.1

Case 2: E=100/10=10

In other words, the VPP is 100 times more effective in the second case than in the first. The same formula for effectiveness can be applied to AV search attempts rather than actual mode switches. That is Nswitches is replaced with Nsearches.

The effectiveness value is used to determine the frequency at which to check for intrinsic conduction. That is, when the effectiveness value has been high, the IMD 10 will more aggressively and more frequently check for intrinsic conduction because it has been shown to be of value to this patient. Conversely, when the effectiveness value is low for a given patient, less frequent conduction checks are made because there is less expectation of success.

Furthermore, the effectiveness value E is utilized by the IMD 10 to optimize the VPP settings. That is, based upon other sensor data and/or other patient data such as cardiac output, ejection fraction, stroke volume, heart rate, patient symptoms, cardiac timing parameters or the like, the IMD 10 can determine when the various VPPs are most appropriate and their most appropriate settings for a given physiological situation. For example, if effectiveness E routinely drops during periods of exertion that include elevated heart rates that still fall below the threshold (210), then the IMD may lower the threshold. Similarly, the effectiveness may be very high during sleep and lower during other periods. Thus, the IMD 10 may be more aggressive in employing the VPP during the night and less aggressive during the day for a given patient.

The effectiveness value is also useful to a physician programming the IMD 10 as the value forms a basis by which therapies and/or settings may be suggested by an analysis of the information or by automated evaluation of collected data. Often, this will be patient dependant. For example, in an otherwise healthy patient an efficiency value of 0.1 (e.g., saving 10 ventricular paced events per switch, on average) would be beneficial, but might not be critical.

Conversely, in a heart failure patient such a reduction in ventricular pacing may be extremely beneficial, thus suggesting more aggressive use of the VPP.

Similarly, the collection of efficiency values over time will illustrate trends for a given patient. That is, the available VPPs may maintain a level of effectiveness over time and thus, their selection will remain appropriate. Alternatively, a patient's condition may change or deteriorate and the VPP might be come less effective, as evidenced by a downward trend in the efficiency value. If this occurs, the frequency of conduction checks could be reduced accordingly. Conversely, if efficiency is trending upward, then that frequency might be increased to further exploit the benefits of the VPP.

Figure 8:
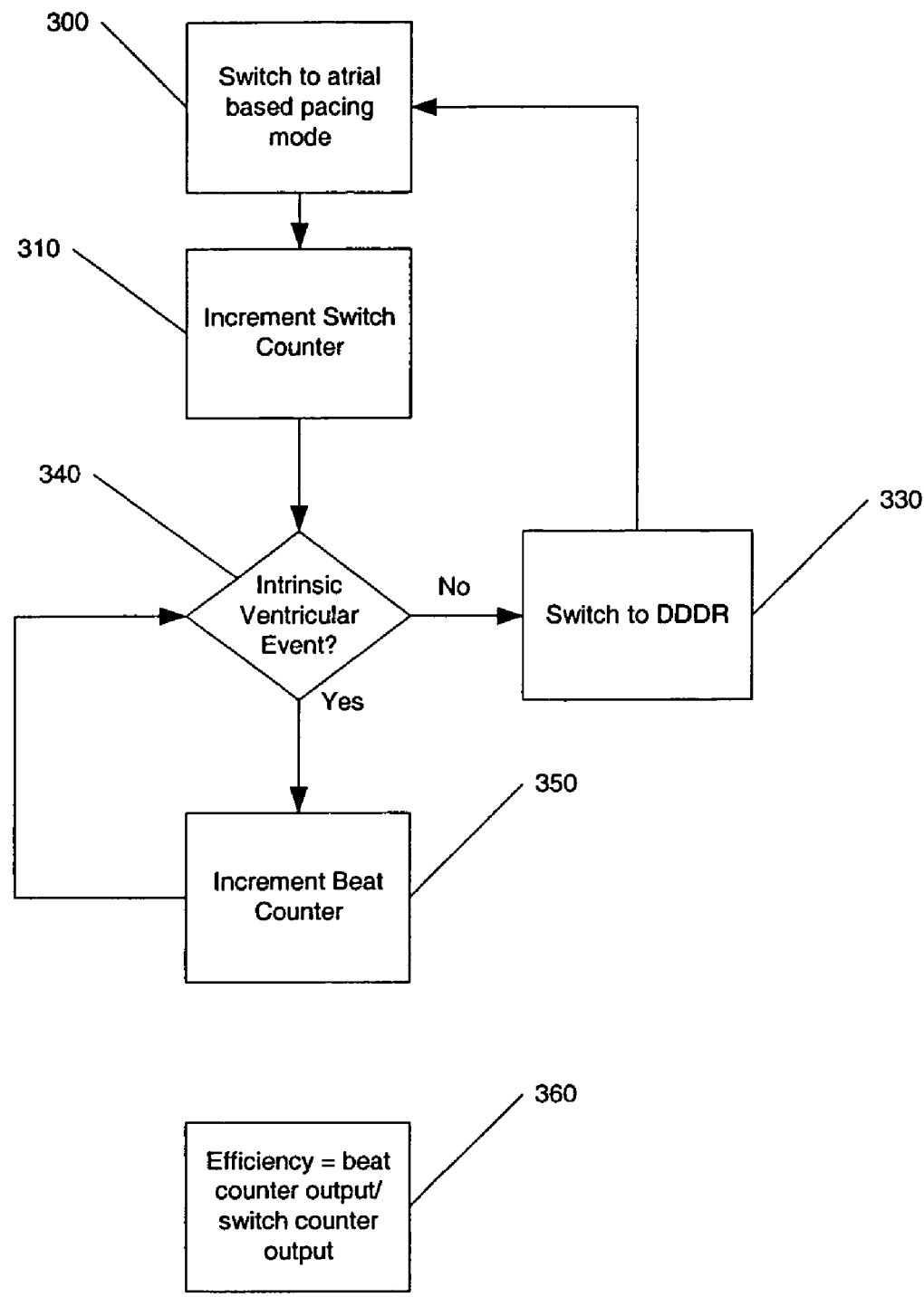
FIGS. 8-9 are flowcharts illustrating processes for determining efficiency within a VPP.

FIG. 8 is a flowchart that illustrates the process for determining efficiency (E) for a VPP over a given time period. At some point in time, the IMD 10 switches (300) into the atrial based pacing mode. Due to this event, a switch counter is incremented (310). Over the course of the cardiac cycle, the IMD 10 monitors (340) for intrinsic ventricular activity. If ventricular activity is sensed, the cycle in considered successful and a (successful) beat counter is incremented (350). The IMD 10 returns to monitoring for intrinsic ventricular events (340) in subsequent cycles. If during any such cycle, there is no sensed ventricular activity, then the IMD 10 mode switches to, e.g., DDDR (330) and delivers a ventricular pace if necessary. Whether on the next cycle or at some subsequent time, the IMD 10 will attempt to return to the atrial based pacing mode (300). This will likewise increment (310) switch counter by one and the process is repeated.

When an efficiency value is desired (360), the output value from the beat counter is divided by the output value of the switch counter. The calculated value is the efficiency E for the relevant time period. The relevant time period is the total number of cycles that have occurred since resetting the values to zero for the switch counter and the beat counter. Alternatively, the relevant time period is a given period of time based on the internal clock circuit of the IMD 10. In this manner, the values for the switch and beat counters can be correlated to a fixed time and efficiency values (E) can be calculated for relevant time periods of varying lengths.

Figure 9:
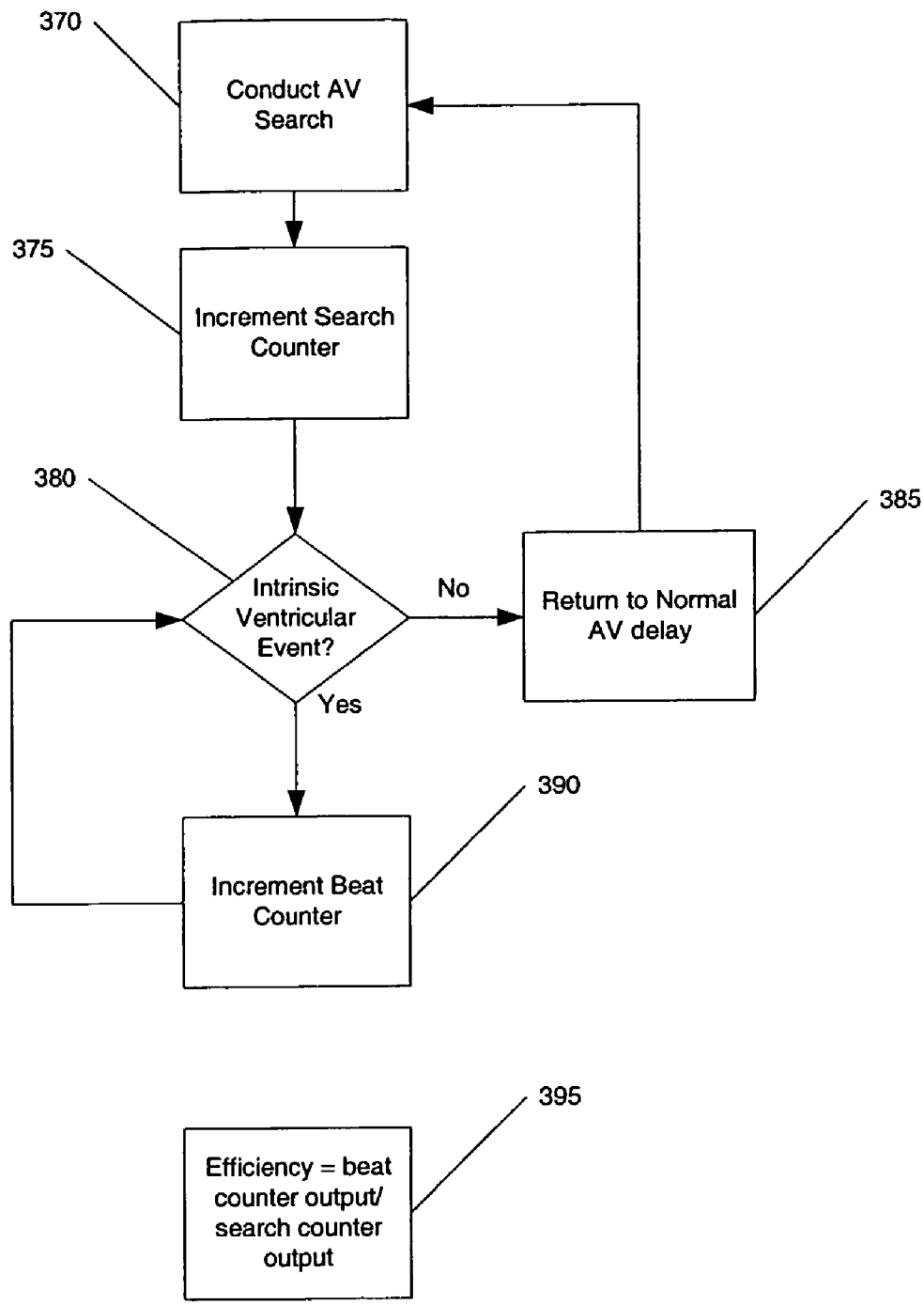

FIG. 9 illustrates a process similar to that of FIG. 8, for calculating the efficiency of AV search attempts. At some point in time, the IMD 10 extends (370) the AV delay to determine in intrinsic conduction is present. Due to this event, an search counter is incremented (375). Over the course of the AV delay, the IMD 10 monitors (380) for intrinsic ventricular activity. If ventricular activity is sensed, the cycle in considered successful and a (successful) beat counter is incremented (390). The IMD 10 returns to monitoring for intrinsic ventricular events (380) in subsequent cycles. If during any such cycle, there is no sensed ventricular activity during the AV delay, then the IMD 10 delivers a ventricular pace at the end of the AV delay. The IMD 10 will then take a subsequent step in the AV search process, such as returning to the normal AV delay (385). At some future time, the IMD 10 will again conduct an AV search (370). This will likewise increment (375) search counter by one and the process is repeated. Though not separately shown, the subsequent step may be to further extend the AV delay at (385), rather then returning to the normal, shorter AV delay. In this manner, progressively long AV delays may be attempted up to a maximum delay.

When an efficiency value is desired (395), the output value from the beat counter is divided by the output value of the search counter. The calculated value is the efficiency E for the relevant time period.

Another consideration in optimizing VPP and pacing in general is the effect of an elevated atrial rate on cardiac output. In an atrial based pacing mode, where ventricular pacing is generally not provided, an elevated pacing rate might not lead to higher cardiac output. Cardiac output is the measure of blood pumped for a given period of time. The components of cardiac output include heart rate and stroke volume. These two components are not necessarily independent of one another and stroke volume is not as dynamically variable as heart rate. An increase in rate often reduces the stroke volume because of reduced filling times. With respect to heart rate, Wenckebach block may also occur, thereby reducing the effective ventricular rate despite an increase in the atrial rate. In addition, the heart requires more energy at the higher rate, thus increasing its own demand for oxygenated blood. Therefore, in order for an elevated pacing rate to beneficially increase cardiac output, the increase gained from the rate component must offset the reduction in stroke volume and higher physiological demands that result.

In response to an elevated heart rate (paced or intrinsic), the AV node should normally adjust the AV delay to ensure proper timing, i.e. the AV delay becomes shorter as heart rate increases. In some patients, this does not occur or the delay actually increases and in either case, the AV delay may become excessively long with respect to the rate. This might result from a deficiency in the autonomic response mechanism, the AV node, or along the conduction pathway. Furthermore, since an artificial sensor perceives the demand for rate response or programming functionality increase rate artificially (e.g., preventive pacing parameters such as atrial overdrive pacing), the autonomic response, even if functional, might not affect the AV node with sufficient speed.

As the AV delay increases (relative to the A-A interval), the VA delay correspondingly decreases. When the VA becomes too short (VA encroachment) for a prolonged period of time, negative effects may result. The ventricles may be fully contracted when the subsequent atrial contraction occurs. Alternatively, the ventricles may be only partially relaxed during that subsequent atrial contraction. The result is that stroke volume is moderately to severely reduced, Wenckebach block occurs, and/or atrial pressures may increase. When this occurs, the elevated atrial rate does not actually increase cardiac output and may in fact reduce it. This issue is of concern in two circumstances. The first is where there is a physiological need for an elevated pacing rate (e.g., activity sensor indicates exercise), but a problem exists that prevents proper intrinsic AV delay timing. The other circumstance is where the pacing rate is non-physiologic; that is, a preventive pacing regime such as atrial overdrive pacing or when the rate response is misinterpreting sensory input to increase demand. In these cases, the AV node might not reduce the AV delay or may actually lengthen the intrinsic AV delay. Thus, the benefits sought by a non-physiologically determined rate (e.g., overdrive pacing) might still be obtained; however, the other issues presented may also result.

FIG. 10 is a flowchart illustrating VPP response to sensed AV delay parameters. The IMD 10 monitors (400) the atrial rate, whether sensed or paced. While the following process has applicability in other situations, this embodiment is described with respect to the IMD 10 operating in a VPP and utilizing an atrial based pacing mode. The IMD 10 determines if the atrial rate is elevated (405). Such an elevation may occur due to physiologic need, perceived physiologic need (e.g., activity sensor), non-physiological pacing regimes (e.g., overdrive pacing), or various arrhythmias or other conditions. While not explicitly limited, if the elevation occurs due to an arrhythmia such as atrial flutter or atrial fibrillation, other mechanisms are typically used to respond.

The IMD 10 monitors (410) the duration of the intrinsic AV delay. That is, the interval from the paced or sensed atrial event to the sensed ventricular depolarization. Of course, such monitoring may occur continuously, but for purposes of the present process, is referred to when the atrial rate is elevated (405).

The IMD 10 will determine (415) if the monitored AV delay is too long for the current rate. In one embodiment, the AV delay is considered too long if its duration exceeds the duration of the AV delay at a lower atrial rate. That is, if the AV delay increased when the atrial rate increased, then the longer AV delay is deemed problematic. In another embodiment, the AV delay is consider too long if it is equal to or longer than the AV delay at a lower atrial rate. In another embodiment, the AV interval is deemed too long if the corresponding VA interval falls below a predetermined threshold. Such a threshold may be a programmed value on the order of 100, 125, 150, or 200 ms or longer. In another embodiment, the acceptable AV delay is determined based upon a look-up table or formula correlating atrial rate with acceptable AV delay programmed into the IMD 10.

If the IMD 10 determines the AV delay is acceptable for a given atrial rate, then the device will continue to monitor (410) the intrinsic AV delay until the atrial rate has returned to the lower value. If the AV delay is deemed too long, then the IMD 10 will take action (420) in response. One or more of the following options may be taken as the responsive action (420), either based upon user programmable selections or device determination.

For any given cardiac cycle, the subsequently scheduled atrial pace may be delayed (425) by a fixed value or by a fixed value (430) along with a safety margin. Effectively, this will elongate the VA interval in the present cycle. The length of the delay for the atrial pace may be a fixed value anytime it is employed or a value corresponding to the elevated atrial rate (405). That is, if the atrial pace is delayed, the fixed value may be, for example, 30 ms. Alternatively, different delay times are available depending upon the atrial rate. Rather than using a fixed value, the IMD 10 may make a dynamic determination as to when to permit the scheduled atrial pace. That is, the intrinsic ventricular event is sensed and then the atrial pace is permitted to occur. By delaying the subsequent atrial pace, many of the issues presented above are addressed. That is, a sufficient interval is provided between the ventricular depolarization and the subsequent paced atrial event. Such a modification will have the effect of altering the atrial rate, but is not an adjustment of the atrial rate per se. In other words, the effective atrial rate may vary on a beat-to-beat basis; an action is taken during a cardiac cycle to affect that cycle; and/or intrinsic ventricular timing affects subsequent atrial pacing.

Another action that can be taken is to reduce (435) the actual atrial-pacing rate. This may be done in lieu of or in addition to delaying an atrial pace for a current cycle. For example, the IMD 10 may delay one or more atrial paces and then if required, lower the overall atrial rate. Alternatively, the atrial rate is lowered without delaying a scheduled atrial pace for the current cycle.

In lowering the atrial rate, the A-A interval is extended in duration and is uniform over time. Thus, a given AV interval will correspond to a smaller percentage of the A-A interval and similarly provide for a longer VA interval. Typically, an adjustment to the atrial rate will take effect in a cycle subsequent to that when the change is implemented, whereas delaying an atrial pace would affect the current cycle and could result in varying A-A intervals over a short span if the overall programmed atrial rate remains the same. In other words, a delayed atrial pace is a variance from the programmed atrial rate that will affect the achieved pacing rate for a small number of cardiac cycles whereas changing the programmed pacing rate is a global change.

The atrial rate may be reduced (435) to the resting rate (445) or to some intermediate value (450) between the resting rate and the current elevated atrial rate. The value chosen will depend upon the pacing methodology responsible for the elevated rate. For example, with atrial overdrive pacing, a determination has been made that an elevated pacing rate will be therapeutic in response to some sensed parameters. Thus, the decision is whether to now forgo overdrive pacing and return to a resting rate (or sensor rate) or conduct or attempt to conduct overdrive pacing at a rate lower than the current elevated atrial rate.

In making such determinations, the relevant data is stored (440) in memory and may be telemetered to an external device for physician review. This data can provide guidance as to what atrial rates lead to prolonged AV intervals for a given patient. In response, this data can be used to alter or decrease the slope (as one possible parameter) of the rate response for a device. That is, as the activity sensor indicates a perceived need for cardiac output, the resultant elevation in the atrial pacing rate is proportionally lower after the modification to rate response.

The predetermined rate of a pacing regime can be lowered (460). For example, for atrial overdrive pacing, one regime may cause the atrial rate to increase 20 bpm over the sensed rate. After an adjustment based upon the data (440), overdrive pacing will occur at a rate 10 bpm over the sensed rate, for example. In addition, the new value can be iteratively determined based upon multiple attempts that result in stored data (440). In the overdrive example, the overdrive pacing rate may be adjusted from a 20 bpm increase to a 15 bpm increase. The IMD 10 may determine when implementing overdrive pacing at 15 bpm, that the AV interval is longer than desired. Thus, overdrive pacing is again modified to a 10 bpm increase. In other words, the adjustments need not be predetermined or static but may be dynamically determined based on patient data.

As another response to the stored data (440) a pacing parameter other than rate may be modified. For example, the threshold values for determining when to enable overdrive pacing can be adjusted to reduce the occurrence of that therapy. Similarly, such a regime may be disabled (470). That is, overdrive pacing, rate response or similar therapies or processes may be selective disengaged to prevent their use will the VPP is in effect.

Another action that the IMD 10 may take (420) is to terminate, on a short or long term basis, the VPP. For example, the IMD 10 may mode switch (475) to DDD or DDDR. If desired, the VPP can be modified so as to include the parameters discussed; that is, the determination of the AV delay when the atrial rate is elevated. When the AV delay is longer than permitted, then the VPP will treat the determination in the same manner that a loss of conduction is treated and switch from the atrial based pacing mode to a dual chamber pacing mode until such time as a conduction check is warranted. The timing with respect to when to conduct a subsequent conduction check may be identical to that used for loss of conduction or may be modified so perform the conduction check only when the atrial rate has lowered to an appropriate level.

In the various embodiments described above, the VPPs seek to promote intrinsic AV conduction, intrinsic ventricular depolarization, and reduce ventricular pacing. In order to do so, the IMD 10 senses ventricular events. In a broad sense, any intrinsic ventricular event sensed between two atrial events meets the above-described criteria and allows the IMD 10 to switch to or remain in the most aggressively permissible configuration of the VPP. For example, when operating in ADIR, any ventricular activity sensed at any time during the A-A interval can be labeled as a ventricular event that indicates AV conduction and ventricular depolarization. In many cases, this broad categorization functions efficiently and effectively.

It should be appreciated that not all sensed ventricular activity represents properly conducted, synchronous ventricular depolarization. For example, a premature ventricular contraction (PVC) or a nodal rhythm may occur. When sensed by the IMD 10, such improper events meet the broad definition of a ventricular event occurring between two atrial events. However, these improper ventricular events contribute less hemodynamically than properly conducted beats. Thus, the present invention provides a mechanism to address improper ventricular events in the context of a VPP.

Various mechanisms are available to determine whether a ventricular event is a properly conducted event or an improper event such as a PVC or nodal rhythm. The timing of the event within an interval (certain windows of time are more likely to indicate a PVC), the lack of a preceding sensed P wave (more likely to indicate an ectopic depolarization), a minimal interval between the atrial event and the sensed ventricular event (nodal rhythms may occur very proximate to atrial events), or the analyzing morphology and/or form of the sensed ventricular event or any combinations of these methods are all techniques available to discriminate between properly conducted ventricular beats and improper beats. U.S. Pat. No. 6,029,087 issued to Wohlgemuth on Feb. 22, 2000 and assigned to Vitatron, B V is herein incorporated by reference in its entirety. The '087 patent illustrates various techniques for identifying sensed events based upon morphology or form parameters and especially in the context of a digital IMD 10 having digital signal processing capabilities. For purposes of the present invention, improper ventricular events may be identified by any of these known techniques.

Figure 11A:
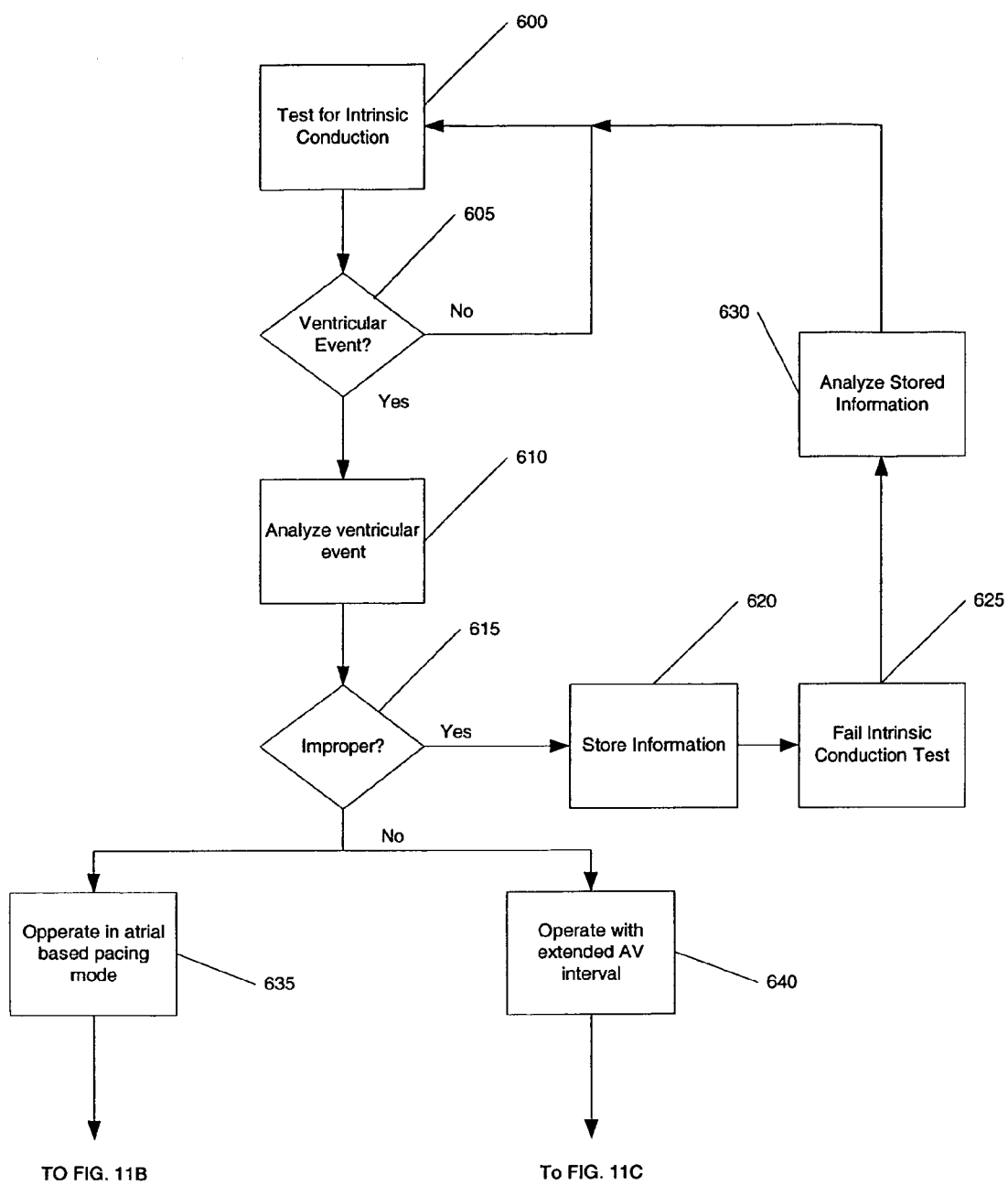
FIGS. 11A-11C are flowcharts illustrating a process for VPP response to improper ventricular events.

FIG. 11A is a flowchart that illustrates a process for addressing sensed improper ventricular events. While operating in the VPP, the IMD 10 will periodically check (600) for intrinsic conduction, as previously explained. The IMD 10 will determine if any ventricular event occurs (605) during the appropriate time frame. If no ventricular event is sensed (605), the VPP will operate according to the appropriate parameters, and may at some point in the future retest for intrinsic conduction (600). It should be appreciated that the VPP may cease subsequent conduction checks and/or may permanently exit the VPP in certain circumstances, though this is not illustrated in the flowchart.

If the IMD 10 senses a ventricular event (605) the IMD 10 will analyze (610) that event to determine if it is properly conducted. As used herein, a regular ventricular event means a properly conducted ventricular depolarization. An improper ventricular event, as used herein means sensed ventricular activity that was not properly conducted or is improperly timed. Such improper ventricular events include PVCs, nodal rhythms and the like. If the sensed ventricular event is deemed to be regular (615), then the intrinsic conduction check (600) is ruled successful and the VPP will operate in the atrial based pacing mode (635) or in a dual chamber mode (640) with an extended AV interval (e.g., mild VPP) and proceed as previously discussed.

If the IMD 10 determines that the sensed ventricular event was improper (615), then this information is stored in memory (620). Furthermore, the intrinsic conduction test (600) is deemed failed 625; thus, the VPP will continue to operate in DDDR, for example. The IMD 10 analyzes (630) the information stored in memory regarding conduction checks failed due to improper ventricular events. Based upon this analysis, subsequent operation in the VPP may be modified. For example, if the improper sensed events tend to occur whenever the AV interval is permitted to extend beyond a given quantity, the VPP may modify the maximum permitted AV interval to avoid improper ventricular events. If improper ventricular events are sensed each time a conduction check occurs, then the VPP may reduce the number of conduction check or may cease to perform them. In addition, more patient specific parameters may be determined. For example, the analyzed data may indicate that conduction checks fail for improper ventricular events, if attempted within 30 minutes of an elevated heart rate above some threshold. Again, the VPP will modify the protocol to avoid conducting the conduction check in that time frame; or, as in all of these examples, may simply report such information to the physician or patient who may then alter the VPP parameters.

Figure 11B:
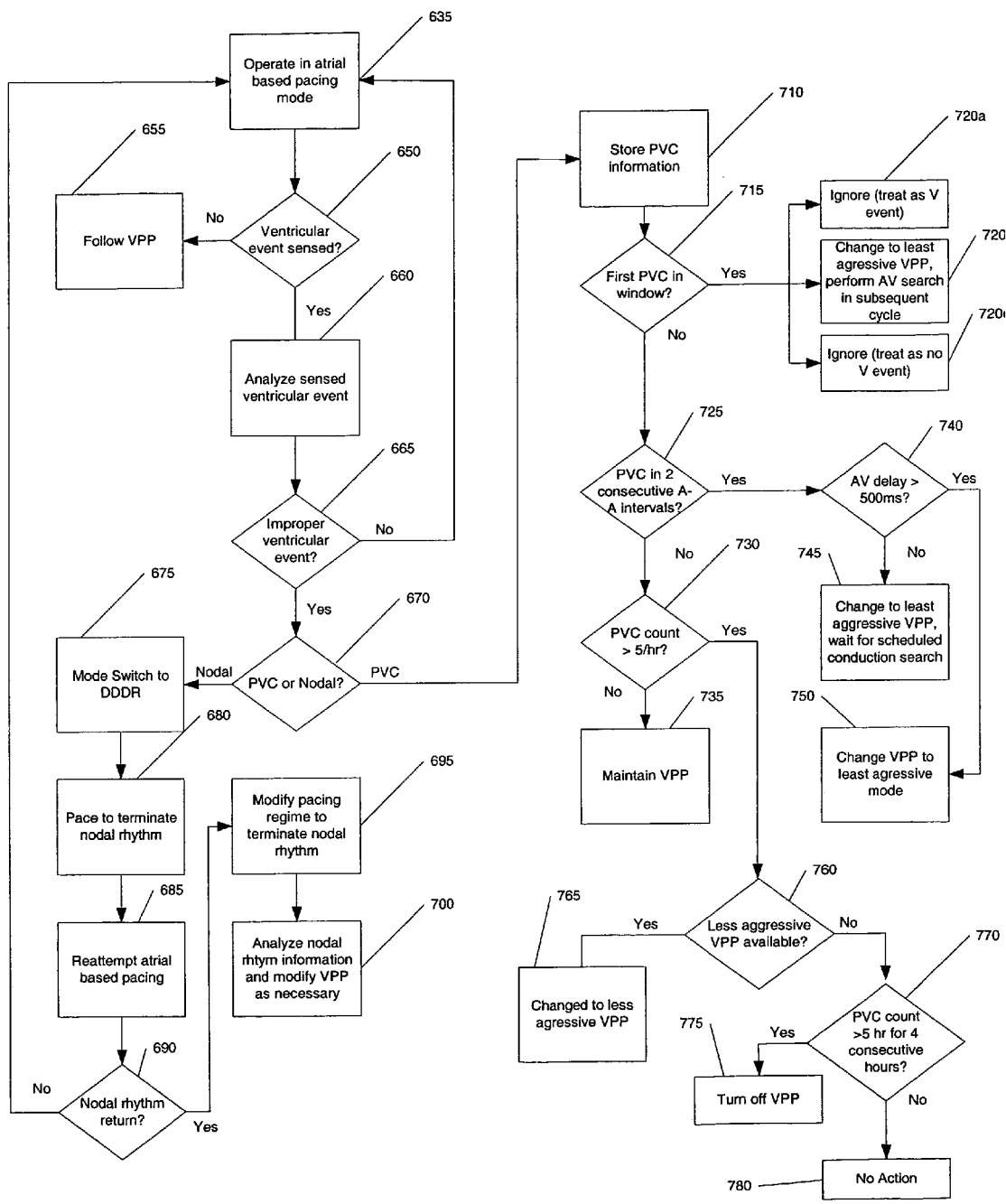

FIG. 11B illustrates the VPP when operating in the atrial based pacing mode (635). For each cardiac cycle, the IMD 10 will sense for ventricular activity (650) over the course of the entire cycle; that is, ventricular pacing is not provided. If no ventricular event is sensed, then the VPP will follow the appropriate parameters (655), as previously discussed. For example, the IMD 10 may mode switch to DDDR for one cycle to provide ventricular pacing capabilities. If there is a ventricular event sensed (650), then the IMD 10 will analyze (660) that ventricular event to determine (665) whether it is improper. If the ventricular event is determined to be a properly conducted one, then the process returns to (635) and the IMD 10 continues to operate in the atrial based pacing mode (635).

If the ventricular event is improper (665), the IMD 10 will then respond depending upon the nature of the improper ventricular event. Two classifications are illustrated and are generally representative. In this embodiment, the IMD 10 determines (670) whether the improper ventricular event is either a PVC or a nodal rhythm. Of course, this determination may be made as part of the analysis (660) or at a separate processing point.

If the ventricular event is a nodal rhythm (670), then the IMD 10 will mode switch to a dual chamber mode such as DDDR (675). An appropriate pacing therapy is delivered (680). For example, increasing the atrial pacing rate and controlling atrial timing terminate the nodal rhythm that is being generated within, e.g., the AV node. As proper timing is restored, normal AV conduction and timing should return. After completion of the pacing therapy, the IMD 10 attempts to return to the atrial based pacing mode (685). If the nodal rhythm does not return, then the IMD 10 continues to operate in the atrial based pacing mode (635). If the nodal rhythm does return, then the IMD 10 provides (695) the appropriate pacing therapy to terminate the nodal rhythm. In this instance, the pacing regime is modified based upon the previous unsuccessful attempt. For example, the duration of the pacing therapy may be increased.

The IMD 10 will analyze (700) the nodal rhythms and the attempts at therapy and either make or suggest (e.g., provide information to a physician) changes to the VPP as necessary. For example, nodal rhythms may always result in the absence of ventricular pacing for a given patient or if the atrial rate falls below a certain level; as such, the VPP may be set to the mild level or disabled and this could be made rate dependent. Alternatively, as indicated above, the patient may be more prone to such nodal rhythms at specific times, such as during or following periods of elevated heart rate. Thus, the VPP may operate in the mild setting during these times. The number of attempts to terminate the nodal rhythm required to make or suggest a given modification can be programmed accordingly.

If the IMD 10 determines (670) that the improper ventricular event is a PVC, that information is stored in memory (710). The IMD 10 then determines if this is the first PVC in a given window (715). The window is the relevant time frame for consideration of PVCs and may be set accordingly. In general, sporadic PVCs are non-problematic. The window defines the period during which multiple PVCs are sufficiently proximate one another that they may be problematic and at least warrant further analysis. Thus, the window will typically be on the order of minutes, hours or multiple hours. In the present embodiment, the window includes the previous four hours.

If the sensed PVC is the first in the window, then the IMD 10 effectively ignores (720a) the classification of improper and treats the ventricular event (in this instance) as a regular ventricular event for purposes of the VPP. Even though a PVC is not as hemodynamically beneficial as a properly conducted event or a paced event, the ventricles do contract and provide cardiac output. While this first PVC is treated as a regular ventricular event in determining subsequent action, the IMD 10 has identified this as a PVC which will affect the process if additional PVCs are sensed during the window.

In an alternative embodiment, the IMD 10 will respond to the first PVC in the window by changing (720b) to the least aggressive VPP. In the next cycle operated in this least aggressive VPP, the IMD 10 performs a conduction check according to the above described process. Thus, even if the PVC was a sporadic event, action is taken and in the next cycle ventricular pacing is available. Since the conduction check is performed immediately thereafter, the infrequent or isolated PVC will not lead to significant ventricular pacing. Alternatively, this conduction check may occur after some predetermined amount of time or number of cycles, rather than in the immediately subsequent cycle.

In another alternative embodiment, a first sensed PVC is ignored (720c) entirely. That is, the VPP will respond to this PVC in the same manner it would respond if no ventricular activity were sensed. Of course, the ventricular event is sensed, classified as a PVC, and data indicating the same is retained.

Thus, the physician programmer can choose how the VPP will respond to the first sensed PVC in a window by either treating it as a conducted event, treating it as if no ventricular event occurred, or by taking an intermediate response with a rapid return to the standard VPP attempted. Alternatively, the IMD 10 may select which response to provide based on attempting the various responses and determining for a given patient the most successful outcome.

If the PVC is not the first in the current window (715), then the IMD 10 proceeds to determine if PVCs are occurring in consecutive cardiac cycles (725). If the current PVC was preceded by a PVC in the previous cycle, then the IMD 10 determines (740) if the AV delay is greater than 500 ms. If the AV delay exceeds this threshold, the presumption is that PVCs are occurring because this delay is excessive. In response, the VPP is changed to the least aggressive (750) setting or the AV delay can be shortened. If PVCs are occurring within 500 ms or less from the atrial event, then the cause of the PVC is not necessarily an AV interval that is too long. As such, the VPP is changed (745) to the least aggressive mode and at the appropriate time a conduction check is performed. If successful, the VPP can then revert to the previous level of aggressiveness. Optionally, the atrial rate may be increased in order to avoid subsequent PVCs in some cases.

If the current PVC is not the first in the window, but does not consecutively follow a cardiac cycle with another PVC, then the IMD 10 determines (730) how many PVC have occurred over a given time period. In this example, the IMD 10 determines whether there have been fewer than five PVCs in the previous hour. If not, then the IMD 10 labels the PVC as intermittent (735) and maintains the VPP in its current form. Though not illustrated, the IMD 10 may respond to this PVC in the same manner available for a first PVC detected in a window and undertake any of steps 720a, 720b, or 720c.

Conversely, if the current PVC causes the PVC count to exceed the threshold, e.g., five or more, then the IMD 10 determines (760) if a less aggressive VPP is available. If so, the VPP is changed to a VPP that is less aggressive. If the VPP is currently in the least aggressive setting (760), then the IMD 10 determines whether this PVC count threshold has been exceeded (770) for some period of time. In this embodiment, the IMD 10 determines if there have been five or more PVCs per hour for the last four consecutive hours. If this level has not been reached, the IMD 10 continues to operate (780) in the least aggressive VPP. Conversely, if PVC have been occurring at a rate of five or more per hour for the last four consecutive hours, then the VPP is disabled (775) and the IMD 10 operates in a standard mode such as DDDR.

Figure 11C:
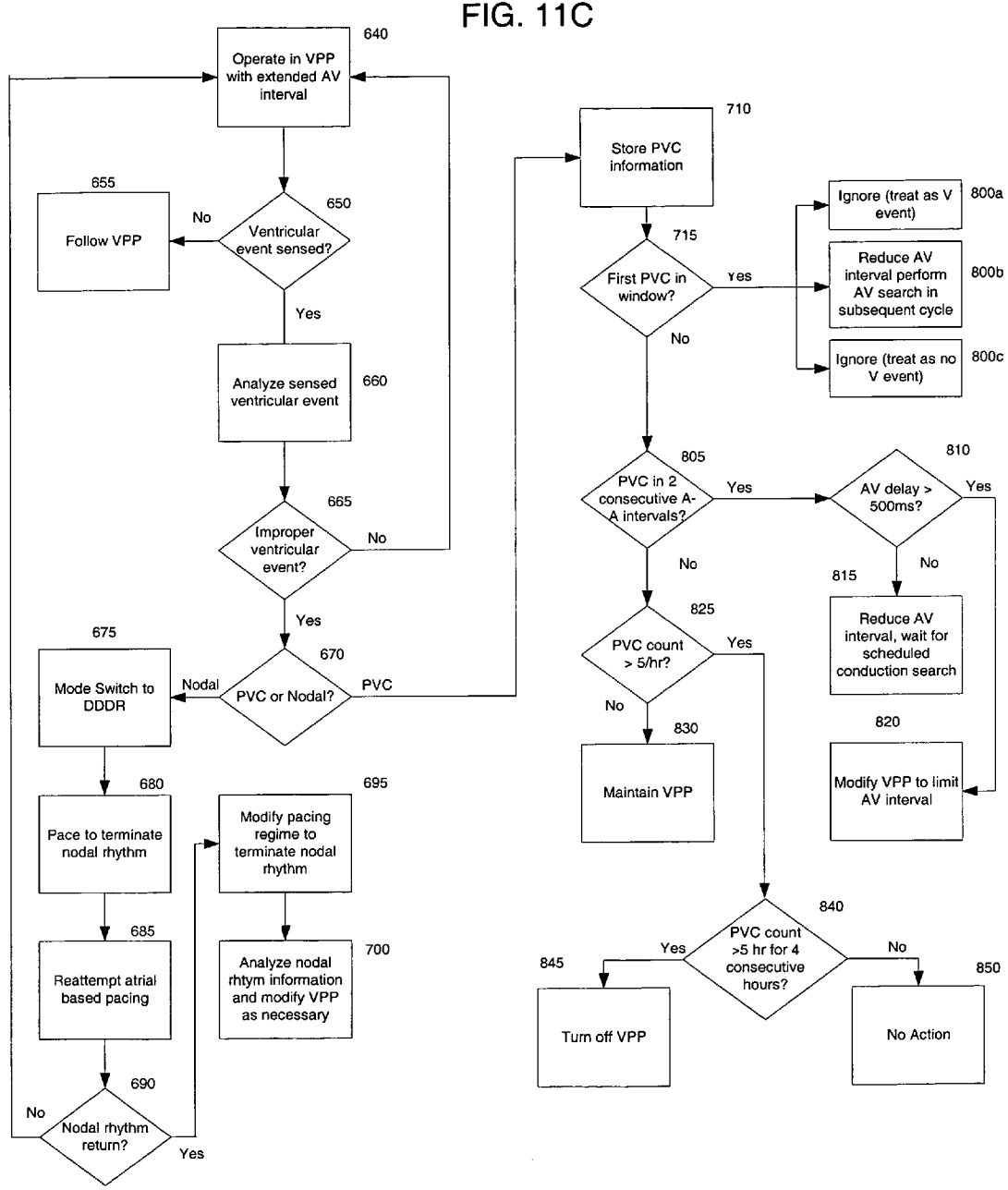

FIG. 11C illustrates a process for responding to improper ventricular events when the initial VPP is operating with a level of aggressiveness that provides for an extended AV interval, but not atrial based pacing. The process is substantially similar to that of FIG. 11B and only the differences will be discussed.

At (800b) and (815), the AV interval is reduced since the VPP is already in a setting where atrial based pacing is precluded. Similarly, at (820) the maximum permitted AV interval is reduced when the PVC occurs after an AV delay of 500 ms or greater.

It should be appreciated that the VPPs as described herein perform certain functions in response to the nature of sensed cardiac activity. To facilitate explanation, these functions are sometimes described as switching from, e.g., an atrial based mode to a dual chamber mode. Various embodiments will function in exactly that manner; that is, the operating mode of the implantable device will switch from one cycle to the next under the control and direction of the VPP. In other embodiments, the same effect is achieved without switching modes in the traditional sense. That is, an entirely new mode is provided that provides the same behavior or effects as described within the rules for this new modality. Thus, device operation will change from one cycle to the next, but the mode does not technically change. For example, such a modality is described in U.S. patent application Ser. No. 10/814,692, filed on Mar. 31, 2004 and titled Fully Inhibited Dual Chamber Pacing Mode, which is herein incorporated by reference in its entirety.

This application is intended to cover any adaptation or variation of the present invention. It is intended that this invention be limited only by the claims and equivalents thereof.

What is claimed is:

1. A method comprising:
    operating an implantable medical device with a Ventricular Pacing Protocol (VPP) that selectively operates in an atrial based pacing mode and a dual chamber pacing mode;
    performing a conduction check to determine if intrinsic conduction is present and if so, operating in the atrial based pacing mode;
    recording an indication each time a conduction check is performed to provide a count total equating to the number of conduction checks performed within a given time period;
    monitoring a number of cardiac cycles operated in the atrial based pacing mode subsequent to each conduction check; and
    calculating an efficiency value based on intrinsic cardiac conduction, equal to the number of cardiac cycles operated in the atrial based pacing mode during the given time period divided by the count total.

2. The method of claim 1, wherein the atrial based pacing mode is ADIR and the dual chamber mode is DDDR.

3. The method of claim 1, wherein the atrial based pacing mode is AAI and the dual chamber mode is DDD.

4. The method of claim 1, further comprising:
    evaluating the efficiency value;
    increasing a frequency of the conduction checks if the efficiency value is above a first threshold;
    decreasing the frequency of the conduction checks if the efficiency value is below a second threshold; and
    maintaining the frequency of the conduction checks at a current level if the efficiency value is between the first and the second threshold.

5. The method of claim 1, wherein the conduction check includes operating for one cardiac cycle in the atrial based pacing mode.

6. The method of claim 5, further comprising operating in the dual chamber pacing mode in a cardiac cycle immediately subsequent to the one cardiac cycle if no intrinsic ventricular activity is sensed during the one cardiac cycle.

7. The method of claim 1, further comprising displaying the efficiency value on a medical device programmer.

8. The method of claim 1, wherein the VPP includes a mild level wherein 1:1 atrial-ventricular (AV) synchrony is maintained with an AV interval greater than an AV interval of the dual chamber pacing mode, a moderate level wherein an absence of ventricular activity in a given cardiac cycle is tolerated in the atrial based mode up to a first frequency of occurrence, and aggressive level wherein an absence of ventricular activity in a given cardiac cycle is tolerated in the atrial based mode up to a second frequency of occurrence, wherein the second frequency of occurrence is greater than the first frequency of occurrence.

9. The method of claim 8, further comprising changing the VPP from the aggressive level to the moderate level if the efficiency value is below a first predetermined threshold and changing the VPP from the aggressive level or the moderate level to the mild level if the VPP is below a second predetermined threshold.

10. The method of claim 9, wherein the first and second predetermined thresholds are correlated to a patient's health status.

11. The method of claim 10, wherein the patient's health status includes an indication for heart failure and a severity of heart failure.

12. The method of claim 11, wherein heart failure severity is inversely correlated to the first and second predetermined values.

13. The method of claim 1, wherein the VPP includes a mild level wherein 1:1 atrial-ventricular (AV) synchrony is maintained with an AV interval of the second duration, a moderate level wherein an absence of ventricular activity in a given cardiac cycle is tolerated in the atrial based mode up to a first frequency of occurrence, and aggressive level wherein an absence of ventricular activity in a given cardiac cycle is tolerated in the atrial based mode up to a second frequency of occurrence, wherein the second frequency of occurrence is greater than the first frequency of occurrence.

14. The method of claim 13, wherein the second AV interval is reduced in duration if the efficiency is below a first predetermined value.

15. The method of claim 13, further comprising changing from the second dual chamber mode to the first dual chamber mode if the efficiency value is below a predetermined value.

16. A method comprising:
    operating an implantable medical device with a Ventricular Pacing Protocol (VPP) that selectively operates in an atrial based pacing mode, a first dual chamber pacing mode having a first maximum AV interval of a first duration, and a second dual chamber pacing mode having a second maximum AV interval of a second duration that is greater than the first duration;
    performing a conduction check to determine if intrinsic conduction is present and if so, operating in the second dual chamber pacing mode;
    recording an indication each time a conduction check is performed to provide a count total equating to the number of conduction checks performed within a given time period;
    monitoring a number of cardiac cycles operated in the second dual chamber pacing mode subsequent to each conduction check; and
    calculating an efficiency value, based on intrinsic cardiac conduction, equal to the number of cardiac cycles operated in second dual chamber pacing mode during the given time period divided by the count total.

17. The method of claim 16, further comprising:
    evaluating the efficiency value;
    increasing a frequency of the conduction checks if the efficiency value is above a first threshold;
    decreasing the frequency of the conduction checks if the efficiency value is below a second threshold; and
    maintaining the frequency of the conduction checks at a current level if the efficiency value is between the first and the second threshold.

18. The method of claim 16, wherein the conduction check includes increasing the AV interval from the first duration to the second duration.

19. The method of claim 16, wherein the conduction check includes incrementally increasing the AV interval from the first duration to the second duration.

20. The method of claim 16, further comprising displaying the efficiency value on a medical device programmer.

* * * * *